US007781427B2

(12) United States Patent
Dehnhardt et al.

(10) Patent No.: US 7,781,427 B2
(45) Date of Patent: Aug. 24, 2010

(54) PROCESS FOR PREPARING QUINOLINE COMPOUNDS AND PRODUCTS OBTAINED THEREFROM

(75) Inventors: Christoph Dehnhardt, New York, NY (US); Sreenivasulu Megati, New City, NY (US); Jerry Sun, Blauvelt, NY (US)

(73) Assignee: Wyeth LLC, Madison, NJ (US)

( * ) Notice: Subject to any disclaimer, the term of this patent is extended or adjusted under 35 U.S.C. 154(b) by 1096 days.

(21) Appl. No.: 11/267,448

(22) Filed: Nov. 4, 2005

(65) Prior Publication Data

US 2006/0122385 A1 Jun. 8, 2006

Related U.S. Application Data

(60) Provisional application No. 60/625,300, filed on Nov. 5, 2004.

(51) Int. Cl.
*A61P 25/00* (2006.01)
*A61K 31/551* (2006.01)
*C07D 243/00* (2006.01)
*C07D 471/06* (2006.01)

(52) U.S. Cl. ..................... 514/219; 540/555
(58) Field of Classification Search ............... 514/219; 540/555
See application file for complete search history.

(56) References Cited

U.S. PATENT DOCUMENTS

| 3,158,619 A | 11/1964 | Wagner |
| 3,235,564 A | 2/1966 | Wagner |
| 3,296,252 A | 1/1967 | Frey et al. |
| 3,329,676 A | 7/1967 | Bell et al. |
| 3,335,134 A | 8/1967 | Frey et al. |
| 3,417,101 A | 12/1968 | Bell et al. |
| 3,466,274 A | 9/1969 | DeRidder |
| 3,714,149 A | 1/1973 | Hester, Jr. |
| 3,914,250 A | 10/1975 | Kim |
| 4,880,814 A | 11/1989 | Chu et al. |
| 4,948,897 A | 8/1990 | Riggs |
| 4,997,831 A | 3/1991 | Bays et al. |
| 5,045,545 A | 9/1991 | Bays et al. |
| 5,134,127 A | 7/1992 | Stella et al. |
| 5,376,645 A | 12/1994 | Stella et al. |
| 5,384,330 A | 1/1995 | Dieter et al. |
| 5,565,483 A | 10/1996 | Hewawasam et al. |
| 5,834,454 A | 11/1998 | Kitano et al. |
| 6,090,803 A | 7/2000 | Failli et al. |
| 6,096,735 A | 8/2000 | Ogawa et al. |
| 6,096,736 A | 8/2000 | Ogawa et al. |
| 6,194,407 B1 | 2/2001 | Failli et al. |
| 6,414,144 B1 | 7/2002 | Welmaker et al. |
| 6,503,900 B2 | 1/2003 | Sabb et al. |
| 6,699,852 B2 | 3/2004 | Robichaud et al. |
| 6,720,316 B2 | 4/2004 | McWhorter, Jr. |
| 6,759,407 B2 | 7/2004 | Goebel et al. |
| 6,777,405 B2 | 8/2004 | Barton et al. |
| 6,849,619 B2 | 2/2005 | Robichaud et al. |
| 6,858,604 B2 | 2/2005 | Sabb et al. |
| 7,129,237 B2 * | 10/2006 | Ramamoorthy ............. 514/219 |
| 7,271,162 B2 | 9/2007 | Sabb et al. |
| 7,271,163 B2 | 9/2007 | Sabb et al. |
| 7,271,164 B2 | 9/2007 | Sabb et al. |
| 2002/0055504 A1 | 5/2002 | Chan |
| 2002/0058689 A1 | 5/2002 | Welmaker et al. |
| 2002/0062022 A1 | 5/2002 | Sabb et al. |
| 2002/0086860 A1 | 7/2002 | Sabb et al. |
| 2002/0107242 A1 | 8/2002 | Sabb et al. |
| 2002/0119966 A1 | 8/2002 | Sabb et al. |
| 2002/0128261 A1 | 9/2002 | Sabb et al. |
| 2002/0147200 A1 | 10/2002 | Nilsson |
| 2002/0150616 A1 | 10/2002 | Vandecruys |
| 2002/0183395 A1 | 12/2002 | Argentieri |
| 2003/0050300 A1 | 3/2003 | McWhorter |
| 2003/0091505 A1 | 5/2003 | Fu |
| 2003/0092694 A1 | 5/2003 | Nilsson et al. |
| 2003/0232814 A1 | 12/2003 | Nilsson et al. |
| 2004/0009970 A1 | 1/2004 | Ramamoorthy |
| 2004/0019040 A1 | 1/2004 | Ramamoorthy et al. |
| 2004/0029949 A1 | 2/2004 | Argentieri |
| 2004/0034005 A1 | 2/2004 | Gao et al. |
| 2004/0092502 A1 | 5/2004 | Fevig et al. |
| 2004/0235856 A1 | 11/2004 | McMurray et al. |
| 2004/0235859 A1 | 11/2004 | Adams et al. |
| 2006/0110451 A1 | 5/2006 | Lin et al. |

(Continued)

FOREIGN PATENT DOCUMENTS

EP 0344015 11/1989

(Continued)

OTHER PUBLICATIONS

Chen and Qian, "One-Pot Synthesis of Tetrahydroquinolines Catalyzed by Dy(OTf)3 in Aqueous Solution," *Synthetic Comm.*, 32: 2543-2548, 2002.
Gatta, et al., "Reactions With Anthranilamides. Snythesis of Pyrido[3,2,1-lj]quinazolines, Pyrido[3,2,1-jk]-1, 4-benzodiazepines and Pyrido[3,2,1-kl]-1, 5- benzodiazcones," *Chimica Ther.*, 7: 480-483, 1972.
Gonzalez, et al., "Pictet-Spengler Type Reactions In 3-arylmethylpiperazine-2, 5-diones. Synthesis of Pyrazinotetrahydroisoquinolines," *Tetrahedron*, 60: 6319-6326, 2004.
Katritzky, et al., "Recent Progress in the Synthesis of 1,2,3,4-Tetrahydroquinolines," *Tetrahedron*, 52: 15031-15070, 1996.

(Continued)

*Primary Examiner*—Brenda L Coleman
(74) *Attorney, Agent, or Firm*—Andrea L. C. Robidoux; Emilie Porter Huck; Choate, Hall & Stewart LLP

(57) ABSTRACT

Methods for synthesizing tetrahydroquinoline-containing compounds are provided, along with synthetic intermediates and products associated with such methods.

54 Claims, No Drawings

U.S. PATENT DOCUMENTS

| | | | |
|---|---|---|---|
| 2006/0111305 A1* | 5/2006 | Tong et al. | 514/23 |
| 2006/0122385 A1 | 6/2006 | Dehnhardt et al. | |
| 2007/0004707 A1 | 1/2007 | Ramamoorthy | |
| 2007/0027142 A1 | 2/2007 | Megati et al. | |
| 2007/0088022 A1 | 4/2007 | Feigelson | |
| 2007/0167438 A1 | 7/2007 | Rosenzweig-Lipson | |
| 2007/0225274 A1 | 9/2007 | Jacobsen | |
| 2007/0225277 A1 | 9/2007 | Rosenzweig-Lipson | |
| 2007/0225278 A1 | 9/2007 | Rosenzweig-Lipson | |
| 2007/0225279 A1 | 9/2007 | Rosenzweig-Lipson | |
| 2007/0238725 A1 | 10/2007 | Rosenzweig-Lipson | |
| 2008/0009480 A1 | 1/2008 | Sabb et al. | |
| 2009/0093630 A1 | 4/2009 | Megati et al. | |

FOREIGN PATENT DOCUMENTS

| | | |
|---|---|---|
| EP | 0357417 | 3/1990 |
| EP | 1714963 | 10/2006 |
| EP | 1792629 | 6/2007 |
| JP | 02-040379 | 2/1990 |
| JP | 10-237073 | 9/1998 |
| JP | 2001-89461 | 4/2001 |
| SU | 930902 | 11/1982 |
| WO | WO-90/15058 | 12/1990 |
| WO | WO-91/11172 | 8/1991 |
| WO | WO-94/02518 | 2/1994 |
| WO | WO-96/29316 | 9/1996 |
| WO | WO-97/30999 | 8/1997 |
| WO | WO-97/31000 | 8/1997 |
| WO | WO-98/55148 | 12/1998 |
| WO | WO-99/41240 | 8/1999 |
| WO | WO-99/66934 | 12/1999 |
| WO | WO-99/67219 | 12/1999 |
| WO | WO-00/35922 | 6/2000 |
| WO | WO-00/40226 | 7/2000 |
| WO | WO-00/64899 | 11/2000 |
| WO | WO-00/76984 | 12/2000 |
| WO | WO-00/77002 | 12/2000 |
| WO | WO-01/12602 | 2/2001 |
| WO | WO-01/12603 | 2/2001 |
| WO | WO-01/64246 | 9/2001 |
| WO | WO-02/08186 | 1/2002 |
| WO | WO-02/36596 | 5/2002 |
| WO | WO-02/42304 | 5/2002 |
| WO | WO-02/059124 | 8/2002 |
| WO | WO-02/059129 | 8/2002 |
| WO | WO-03/091250 | 11/2003 |
| WO | WO 03/091250 A1 | 11/2003 |
| WO | WO 03/091251 A1 | 11/2003 |
| WO | WO-03/091257 | 11/2003 |
| WO | WO-03/097636 | 11/2003 |
| WO | WO-2004/072046 | 8/2004 |
| WO | WO-2004/094401 | 11/2004 |
| WO | WO-2005/023243 | 3/2005 |
| WO | WO-2006/052768 | 5/2006 |
| WO | WO-2007/020533 | 2/2007 |

OTHER PUBLICATIONS

Stokker, "Preparation Of 1,2,3,4-Tetrahydroisoquinolines Lacking Electron Donating Groups—An Intramolecular Cyclization Complementary To The Pictet-Spengler Reaction," *Tetrahedron Letters*, 37: 5453-5456, 1996.

Zhang, et al., "Pictet-Spengler Reaction in Trifluoroacetic Acid. Large Scale Synthesis of Pyridoindolobenzodiazepine As An Atypical Antipsychotic Agent," *Tetrahedron Letters*, 36: 8387-8390, 1995.

International Search Report, PCT/US2005/040062, May 2006.

Wilen et al., "Strategies in optical resolutions," *Tetrahedron* 33:2725 (1977).

Bishop et al., "New 5HT$_{2C}$ receptor agonists," *Expert Opin. Ther. Patent* 13:1691-1705 (2003).

Martin et al., "Activity of Aromatic Substituted Phenylpiperazines Lacking Affinity for Dopamine Binding Sites in a Preclinical Test of Antipsychotic Efficacy," *J. Med. Chem.* 32:1052-1056 (1989).

Browning et al., "The Antipsychotic-like Action of a 5-HT$_{2}$c Agonist on Conditioned Avoidance Behavior in Rats," *Society for Neuroscience Abstracts* 25(2): Abstract 830.12 (1999).

Hester et al., "Pyrrolo[3,2,1-*jk*][1,4]benzodiazepines and Pyrrolo[1,2,3-*ef*][1,5]benzodiazepines Which Have Central Nervous System Activity," *J. Med. Chem.* 13: 827-835 (1970).

Kim et al., "Synthesis of 1,2,3,4,8,9,10,11-Octahydro-[1,4]diazepino[6,5,4-*jk*]carbazole and Related Compounds," *J. Heterocycl. Chem.* 13(6): 1187-1192 (1976).

Haerter et al., "Schmidt Reaction on Tetrahydro-Quinolone Derivatives," *Chimia* 30: 50-52 (1976).

Lowry et al., "Protein Measurement with the Folin Phenol Reagent," *J. Biol. Chem.* 193: 265-275 (1951).

Naruto et al., "Photocyclization of N-Chloroacetyl Derivatives of Indolylethylamines to Azepinoindoles and Azocinoindoles. Correlation of the Reactivity of Indole Radicals with Frontier Electron Densities Calculated by Unrestricted Hartree-Fock Mo," *Tetrahedron Lett.* 39: 3399-3402 (1975).

Digiovanni et al., "Preferential Modulation of Mesolimbic Vs. Nigrostriatal Dopaminergic Function by Serotonin$_{2C/2B}$ Receptor Agonists: A Combined In Vivo Electrophysiological and Microdialysis Study," *Synapse* 35: 53-61 (2000).

Dimatteo et al., "Selective blockade of serotonin$_{2C/2B}$ receptors enhances dopamine release in the rat nucleus accumbens," *Neuropharmacology* 37: 265-272 (1998).

Dimatteo et al., "SB 242 084, a selective serotonin$_{2C}$ receptor antagonist, increases dopaminergic transmission in the mesolimbic system," *Neuropharmacology* 38: 1195-1205 (1999).

Millan et al., "Serotonin (5-HT)$_{2C}$ receptors tonically inhibit dopamine (DA) and noradrenaline (NA), but not 5-HT, release in the frontal cortex in vivo," *Neuropharmacology* 37: 953-955 (1988).

Masand, "Weight gain associated with psychotropic drugs," *Exp. Opin. Pharmacother.* 1(3): 377-389 (2000).

Allison et al., "Antipsychotic-Induced Weight Gain: A Comprehensive Research Synthesis," *Am J. Psychiatry* 156(11): 1686-1696 (1999).

Cowen et al., "Hypophagic, Endocrine and Subjective Responses to *m*-Chlorophenylpiperazine in Healthy Men and Women," *Human Psychopharmacology* 10: 385-391 (1995).

Schotte et al., "Risperidone compared with new and reference antipsychotic drugs: in vitro and in vivo receptor binding," *Psychopharmacology* 124: 57-73 (1996).

Fox et al., "Behavioral Effects of 5-HT$_{2C}$ Receptor Antagonism in the Substantia Nigra Zona Reticulata of the 6-Hydroxydopamine-Lesioned Rat Model of Parkinson's Disease," *Experimental Neurology* 151: 35-49 (1998).

Whitaker, "Atypical Antipsychotics: A Modest Advance in Treating Schizophrenia," *Spectrum* 2: 1-12 (2000).

Grinev et al., "Synthesis of New Condensed Heterocycles by the Fischer Method," *Chem. Heterocycl. Compd.* 19(9): 959-961 (1983).

Grinev et al., "Synthesis and Aminomethylation of Derivatives of Pyrazino[3,2,1-*jk*]Carbazole and Diazepeno[3,2,1-*jk*]Carbazole," *Chem. Heterocycl. Compd.* 19(12): 1312-1315 (1983).

Lamanova et al., "Synthesis and Pharmacological Activity of 1,4-Diazepino[3,2,1-hi]-Indoles," *Pharm. Chem. J.* 23(2): 113-115 (1989).

Kim et al., "Derivatives of Tetrahydro-1,4-benzodiazepines as Potential Antihypertensive Agents," *J. Med. Chem.* 20(2): 209-212 (1977).

Toscano et al., "Synthesis and Properties of some Tetracyclic Derivatives of 9*H*-Carbazole, 10,11-Dihydro-5*H*-dibenz[*b,f*]azepine, and 5,11-Dihydrodibenz[*b,e*][1,4]oxazepine," *J. Heterocycl. Chem.* 13: 475-480 (1976).

Katritsky et al., "Synthesis of 3,4,7,8-Tetrahydro-6*H*-pyrido[1,2,3-*et*]-1,5-benzodiazepin-2-(1*H*)-ones via Benzotriazole Methodology," *Synthesis* 10: 1487-1490 (1998).

Gatta et al., "Pirazino(1,2-a)- E 1,4-Diazepino(1,2-a)Indoli," *Edizione Scientifica* 30(8): 631-641 (1975).

Lopes et al., "Synthesis of New Tetracyclic Derivatives of 10H-Phenoxazine, 10,11-Dihydro-5H-Dibenzo[b,f]Azepine and (9)10H-Acridinone Through Isatinic Intermediates," *J. Brazilian Chem. Soc.* 4(1): 34-39 (1993).

Rosenzweig-Lipson et al., "Antiobesity-Like Effects of the Selective 5-HT2C Agonist Way 161503" *FASEB J.* 14: A1321 (2000).

Archer et al., "1-Ethyl-4-(3-tropanyl)-tetrahydro-1H-1,4-benzodiazepine," *J. Am. Chem. Soc.* 79: 5783-5785 (1957).

Zhang et al., "Pictet-Spengler reaction in trifluoroacetic acid. Large scale synthesis of pyridoindolobenzodiazepine as an atypical antipsychotic agent," *Tetrahedron Lett.* 36(46): 8387-8390 (1995).

Stokker, "Preparation of 1,2,3,4-tetrahydroisoquinolines lacking electron donating groups—an intramolecular cyclization complementary to the Pictet-Spengler reaction," *Tetrahedron Lett.* 37(31): 5453-5456 (1996).

Cuadro et al., "Synthesis of N-(Aminoethyl)Azoles Under Phase Transfer Catalysis," *Synth. Commun.* 21(4): 535-544 (1991).

Perkin et al., "Dihydropentindole and its Derivatives, Part I," *J. Chem. Soc.* 123: 3242-3247 (1923).

Booth et al., "Synthetic and Stereochemical Investigations of Reduced Cyclic Bases. Part V.* The Exhausive Methylation of Some Partially Reduced Cyclic Bases," *J. Chem. Soc.* 158: 2302-2311 (1958).

Cowen et al., Why is dieting so difficult? *Nature* 376: 557 (1995).

Robichaud et al., "Recent Advances in Selective Serotonin Receptor Modulation," *Ann. Rep. Med. Chem.* 35: 11-20 (2000).

Hoyer et al., "International Union of Pharmacology Classification of Receptors for 5-Hydroxytryptamine (Serotonin)," *Pharm. Exp. Ther.* 46(2): 157-203 (1994).

Tecott et al., "Eating disorder and epilepsy in mice lacking 5-$HT_{2C}$ serotonin receptors," *Nature* 374: 542-546 (1995).

Kim, "Improved Syntheses of 1,4-Benzodiazepine-2,5-diones," *J. Heterocycl. Chem.* 12:1323-1324 (1975).

Sabb et al., "Cycloalkyl[*b*][1,4]benzodiazepinoindoles are agonists at the human 5-$HT_{2C}$ receptor," *Bioorg. Med. Chem. Lett.* 14: 2603-2607 (2004).

Herrick-Davis et al., "Inverse Agonist Activity of Atypical Antipsychotic Drugs at Human 5-Hydroxytryptamine2C Receptors," *J. Pharm. Exp. Ther.* 295: 226-232 (2000).

Rosenzweig-Lipson et al., "Antidepressant-like effects of the novel, selective, 5-HT2C receptor agonist WAY-163909 in rodents," *Psychopharmacology* 192: 159-170 (2007).

Dunlop et al., "Pharmacological profile of the 5-HT2C receptor agonist WAY-163909; therapeutical potential in multiple indications," *CNS Drug Reviews* 12: 167-177 (2006).

Chen et al., "One-pot synthesis of tetrahydroquinolines catalyzed by Dy(OTf)$_3$ in aqueous solution," *Synth. Commun.* 32: 2543-2548 (2002).

Gatta et al., "Reactions with anthranilamides. Synthesis of pyrido[3,2,1-lj]quinazolines, pyrido[3,2,1-jk]-1,4-benzodiazepines and pyrido[3,2,1-kl]-1,5-bezodiazocines," *Chimica Ther.* 7: 480-483 (1972).

Gonzalez et al., "Pictet-Spengler type reactions in 3-arylmethylpiperazine-2,5-diones. Synthesis of pyrazinotetrahydroisoquinolinones," *Tetrahedron* 60: 6319-6326 (2004).

Katritzky et al., "Recent progress in the synthesis of 1,2,3,4-tetrahydroquinolines," *Tetrahedron* 52: 15031-15070 (1996).

Descamps et al., "Recherches dans la serie des benzofurannes XLII. Synthese de benzofuryl-2 methylamines et d'amides d'acides coumaryliques," *Chime Therapeutique* 5(3): 169-184 (1970).

Posson et al., "Imino Diels-Alder reaction: Application to the synthesis of diverse cyclopenta[c]quinolines derivatives," *Synlett* 2000 (2): 209-12.

Jacques et al., "Dissociable compounds and complexes," *Enantiomers, Racemates, and Resolutions* 378: 257-259 (1991).

Bew et al., "Experiments on the Synthesis of Azasteroids. Part II*," *J. Chem. Soc.* 1775-1777 (1955).

Chrzanowska et al., "Asymmetric Synthesis of Isoquinoline Alkaloids," *Chem. Rev.* 104: 3341-3370 (2004).

Cox et al., "The Pictet-Spengler Condensation: A New Direction for an Old Reaction," *Chem. Rev.* 95: 1797-1842 (1995).

Cui et al., "Catalytic Homogenous Asymmetric Hydrogenations of Largely Unfunctionalized Alkenes," *Chem. Rev.* 105: 3272-3296 (2005).

Maryanoff et al., "Cyclizations of N-Acyliminium Ions," *Chem. Rev.* 104: 1431-1628 (2004).

Ono et al., "Regioselective Synthesis of 8-Hydroxytetrahydroquinolines by the Cyclization of m-Hydroxyphenethyl Ketone O-2,4-Dinitrophenyloximes," *Chem. Lett.* 5: 437-438 (1998).

Royer et al., "Chiral Heterocycles by Iminium Ion Cyclization," *Chem. Rev.* 104: 2311-2352 (2004).

Rozzel et al., "Preparation of Diastereomeric 2-Deuterio-3-Hydroxy Butyrate. A General Method for Hydrogenation of β-Acyloxy-α,β-Unsaturated Crotonates," *Tetrahedron Lett.* 23: 1767-1770 (1982).

Jaroch et al., "Dihydroquinolines as Novel n-NOS Inhibitors," *Bioorg. Med. Chem. Lett.* 12: 2561-2564 (2002).

Tang et al., "New Chiral Phosphorus Ligands for Enantioselective Hydrogenation," *Chem. Rev.* 103: 3029-3069 (2003).

Pribyla et al., "Solubility of Anthracene in Ternary Methyl *tert*-Butyl Ether+Alcohol+2,2,4-Trimethylpentane Solvent Mixtures at 298.15 K," *J. Chem. Eng. Data* 45: 974 (2000).

* cited by examiner

PROCESS FOR PREPARING QUINOLINE COMPOUNDS AND PRODUCTS OBTAINED THEREFROM

CROSS-REFERENCE TO RELATED APPLICATIONS

This application claims priority to U.S. provisional application No. 60/625,300, filed Nov. 5, 2004, the entire contents of which is hereby incorporated herein by reference.

FIELD OF THE INVENTION

The present invention relates to methods for synthesizing tetrahydroquinoline compounds, as well as intermediates and products associated with such methods.

BACKGROUND OF THE INVENTION

International Patent Application WO 03/091250, in the name of Ramamoorthy, discloses tetrahydroquinoline-containing compounds, methods for their preparation, and methods for using them as, for example, psychotic and antiobesity agents. Alternative synthetic methods for these and other tetrahydroquinoline-containing compounds are desired.

SUMMARY OF THE INVENTION

In one aspect, the present invention provides methods for preparing tetrahydroquinoline-containing compounds by reacting benzodiazepines with paraformaldehyde and suitable unsaturated moieties such as alkenes (including dienes) or alkynes. In certain embodiments, the methods of the invention are directed to preparing tetrahydroquinolines and involve reacting benzodiazepine with a solid formaldehyde equivalent, such as paraformaldehyde and an alkene or alkyne in the presence of a Lewis acid and a reaction solvent. Reaction solvents useful for forming such tetrahydroquinoline-containing compounds include polar aprotic solvents such as alkyl nitriles (e.g., acetonitrile, propionitrile and butyronitrile), esters (e.g., ethyl acetate), chlorinated hydrocarbons (e.g., methylene chloride), N-alkyl formamides (e.g., dimethyl formamide), and mixtures thereof.

Certain preferred methods include providing a compound of formula I:

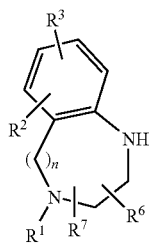

I where:
$R^1$ is alkyl, alkanoyl, aroyl, carboalkoxy, or carboalkoxyaryl;
$R^2$ and $R^3$ are, independently, hydrogen, hydroxy, alkyl, alkoxy, halogen, carboxamido, carboalkoxy, perfluoroalkyl, cyano, alkanesulfonamido, alkanesulfonyl, alkanamido, amino, alkylamino, dialkylamino, perfluoroalkoxy, alkanoyloxy, alkanoyl, aroyl, aryl, arylalkyl, heteroaryl, or heteroarylalkyl;
$R^6$ and $R^7$ are, independently, hydrogen or alkyl;
n is 1 or 2; and contacting the compound of formula I with at least one formaldehyde equivalent and a reagent having either formula $R^4$—CH=CH—$R^5$ or formula $R^4$—C≡C—$R^5$, in the presence of a Lewis acid and a reaction solvent to form a compound of formula II:

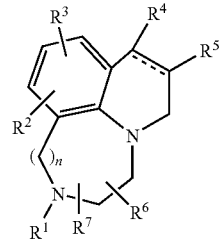

II wherein each of $R^1$, $R^2$, $R^3$, $R^6$, $R^7$, and n are as defined above;
the formaldehyde equivalent is in solid form at some time prior to the contacting;
$R^4$ and $R^5$ are, independently, hydrogen or alkyl of 1 to 6 carbon atoms, or taken together with the carbons to which they are attached, form a cyclic moiety that is cycloalkyl, cycloalkenyl, bridged bicyclic alkyl, bridged bicyclic alkenyl, pyranyl or thiopyranyl in which the sulfur atom is optionally oxidized to the sulfoxide or sulfone; and
the dotted line represents an optional double bond.

Preferred methods of the invention further comprise contacting a compound of formula II with an acid having a pKa less than 1 and forming a bis salt of formula III:

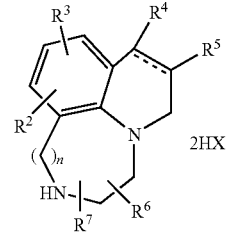

III wherein X is the counterion of the acid such as, for example, halogen, hydrogensulfate, or an alkyl- or aryl-sulfonate.

The methods of the invention further include contacting the bis salt of formula III with base, thereby forming a free base having the formula IV:

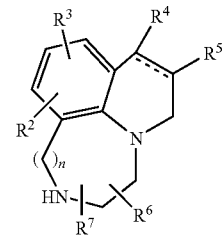

IV

Preferred bases are alkaline metal hydroxides, alkaline earth metal hydroxides, carbonates, phosphates, organic bases, and combinations thereof. Sodium hydroxide in an aqueous solution is particularly preferred. Free bases according to the invention can alternatively be formed by contacting a compound of formula II with a base. Free bases according to the invention can also be prepared by contacting a compound of formula I, where $R^1$ is replaced by hydrogen, with a formaldehyde equivalent and a reagent having either formula $R^4$—CH=CH—$R^5$ or formula $R^4$—C≡C—$R^5$ in the presence of a Lewis acid and a reaction solvent, where the formaldehyde equivalent is in solid form at least prior to the contacting.

The free base of formula IV typically is formed as a racemic mixture. Where a particular enantiomer is preferred it may be provided substantially free of the corresponding enantiomer by isolation or separation methods known in the art including, for example, high performance liquid chromatography and chiral salt resolution, or by techniques described herein.

The racemic compound of formula IV is treated with a chiral agent to form a diastereomeric mixture thereof. In certain embodiments, the racemic compound of formula IV is treated with a chiral acid to form a diastereomeric salt thereof. As used herein, the term "diastereomeric salt" refers to the adduct of a chiral compound of formula IV with a chiral acid. The resulting diastereomeric mixture is then separated by suitable means to obtain a the desired diastereomeric salt. Such suitable means for separating diastereomeric mixtures are well known to one of ordinary skill in the art and include, but are not limited to, those methods described herein. It will be appreciated that, depending upon the chiral acid used, there may be one or more carboxylate moieties present. In certain embodiments, the chiral acid has two carboxylate moities as with, for example, tartaric acid or a derivative thereof.

The term "separated by suitable physical means" refers to methods of separating enantiomeric or diastereomeric mixtures. Such methods are well known in the art and include preferential crystallization, distillation, and trituration, among others. Chiral agents and separation methods are described in detail in Stereochemistry of Organic Compounds, Eliel, E. L. and Wilen, S. H., 1994, published by John Wiley and Sons.

In preferred embodiments, the diastereomeric salts thus formed are contacted with organic or inorganic acid having a pKa lower than the chiral resolving acid to form the desired enantiomeric salt. As used herein, the term "enantiomeric salt" refers to the salt of the resolved chiral compound of formula IV, wherein said compound of formula IV is enriched in one enantiomer. As used herein, the term "enantiomerically enriched", as used herein signifies that one enantiomer makes up at least 85% of the preparation. In certain embodiments, the term enantiomerically enriched signifies that at least 90% of the preparation is one of the enantiomers. In other embodiments, the term signifies that at least 95% of the preparation is one of the enantiomers. Acids for enantiomeric salt formation include hydrochloric acid, sulfuric acid, phosphoric acid, hydrobromic and hydroiodic acid, malic acid, succinic acid, trifluoro acetic acid, acetic acid, methane sulfonic acids, alkyl- and aryl sulfonic acids, and combinations thereof.

Thus, representative enantiomeric salts are those having, for example, formula Va or Vb

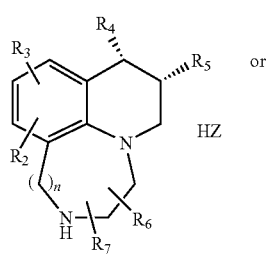

Va

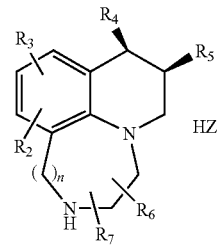

Vb wherein each of $R^2$, $R^3$, $R^4$, $R^5$, $R^6$, $R^7$, and n is as defined above and each Z is a counter ion of the acids mentioned above. Examples of Z include, but are not limited to, halogens such as Cl, Br and I, and ions including $HSO_4$, $H_2PO_4$, MsO (where Ms is mesylate), AcO (wherein Ac is acetyl), maleate, and succinate. Enantiomeric salts once formed are preferably recrystallized to improve purity. Suitable recrystallization solvents include aqueous alcohol such as alkyl alcohols like methanol, ethanol, isopropanol, and butanol. In preferred embodiments, the enantiomeric salt is a compound of formula G:

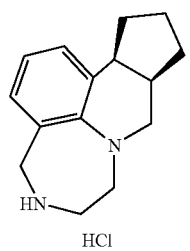

G in greater than about 90 area percent chiral purity, preferably greater than about 95 area percent chiral purity, more preferably greater than about 99 area percent chiral purity (HPLC area percent of desired enantiomer relative to total HPLC area of stereoisomers (enantiomers)). The free base name of compound G is (9aR,12aS)-4,5,6,7,9,9a,10,11,12,12a-decahydrocyclopenta[c][1,4]diazepino[6,7,1-ij]quinoline. The salt as shown in formula G has (−) optical rotation. One skilled in the art would recognize that the optical rotation of G can change if converted to free base form.

The present invention also provides the compounds of formulae I, II, III, IV, G, Va, and Vb and other synthetic intermediates and products produced according to the foregoing methods. Preferably, such compounds are provided in greater than about 90 weight percent purity.

For example, the present invention provides compounds of formula V:

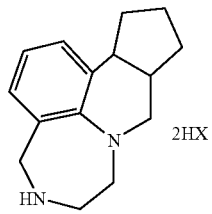

V where X is a counterion of an acid having a pKa less than 1.

The present invention also provides compositions comprising a diastereomeric salt of a diaroyl-L-tartaric acid and a free base of formula VIb:

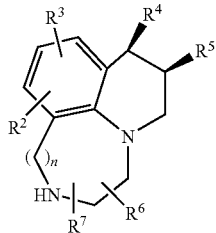

VIb wherein each of $R^2$, $R^3$, $R^4$, $R^5$, $R^6$, $R^7$, and n is as defined above and neither of $R^4$ and $R^5$ is hydrogen.

In other embodiments, compositions are provided that include at least about 90 area percent HPLC of a compound of formula II:

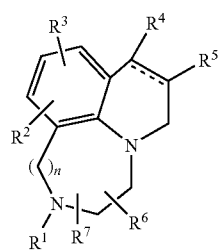

II wherein each of $R^1$, $R^2$, $R^3$, $R^4$, $R^5$, $R^6$, $R^7$, and n is as defined above and a compound of formula VIII:

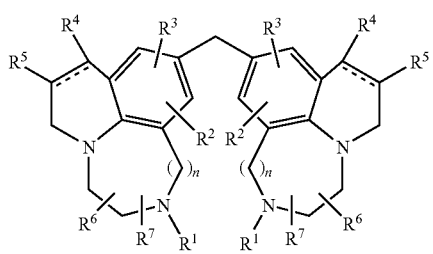

VII in less than an amount of about 10 area percent HPLC.

In yet other embodiments, compositions are provided that include a compound of formula III:

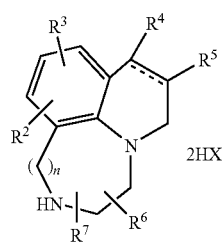

III

2HX wherein each of $R^2$, $R^3$, $R^4$, $R^5$, $R^6$, $R^7$, n, and X is as defined above; and a compound of formula X:

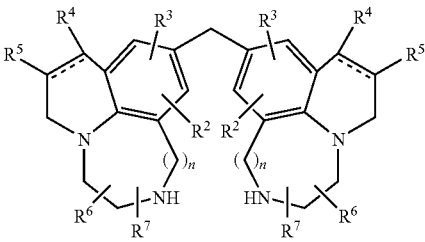

X wherein each of $R^2$, $R^3$, $R^4$, $R^5$, $R^6$, $R^7$, and n is as defined above, or a salt thereof, in less than an amount of about 10 area percent HPLC.

In yet other embodiments, compositions are provided that include a diastereomeric salt of a diaroyl tartaric acid and a free base of formula IV:

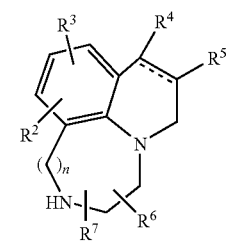

IV wherein each of $R^2$, $R^3$, $R^4$, $R^5$, $R^6$, $R^7$, and n is as defined above, and a compound of formula

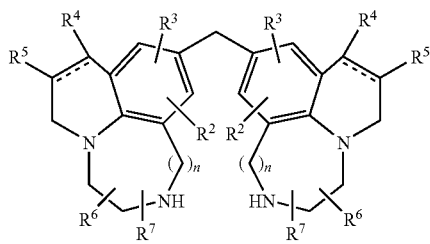

X wherein each of $R^2$, $R^3$, $R^4$, $R^5$, $R^6$, $R^7$, and n is as defined above, or a salt thereof (including diastereomeric salt) in an amount of less than about 10 area percent HPLC.

In further embodiments, compositions are provided that include a compound of formula G

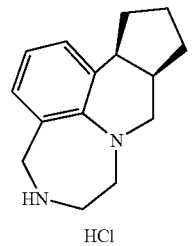

G

HCl and one or more organic impurities in a total amount of about 2 area percent HPLC or less, or one or more residual solvents in a total amount of 1.0 weight percent or less.

Other embodiments provide compositions containing a compound of formula G:

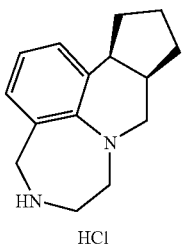

G

HCl and water in an amount of about 2.0 weight percent or less as measured by KF titration, and/or where G has a hydrogen chloride content of from about 12.8 weight percent to about 14.8 weight percent as measured by ion chromatography, based on the total weight of the composition.

Even further embodiments provide a compound of formula G:

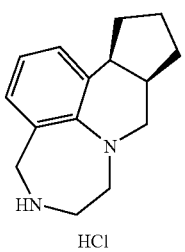

G

HCl in the form of needle shaped crystals and/or having a median particle size of less than about 25.

In yet further embodiments, a method is provided that includes providing a compound of formula VIII:

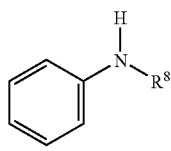

VIII and contacting the compound of formula VIII with at least one formaldehyde equivalent and a reagent having either formula $R^4$—CH=CH—$R^5$ or formula $R^4$—C=C—$R^5$, in the presence of a Lewis acid and a reaction solvent to form a compound of formula IX:

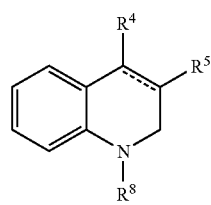

IX where the formaldehyde equivalent is in solid form at least prior to the contacting;
  $R^8$ is a branched or straight chain alkyl group; a hetero-substituted alkyl group; an aryl group or an arylalkyl group; and
  $R^4$ and $R^5$ are, independently, hydrogen or alkyl of 1 to 6 carbon atoms, or taken together with the carbons to which they are attached, form a cyclic moiety that is cycloalkyl, cycloalkenyl, bridged bicyclic alkyl, bridged bicyclic alkenyl, pyranyl or thiopyranyl in which the sulfur atom is optionally oxidized to the sulfoxide or sulfone.

DETAILED DESCRIPTION OF ILLUSTRATIVE EMBODIMENTS

In preferred embodiments, compounds according to the invention are prepared according to the reaction scheme demonstrated below:

Scheme 1

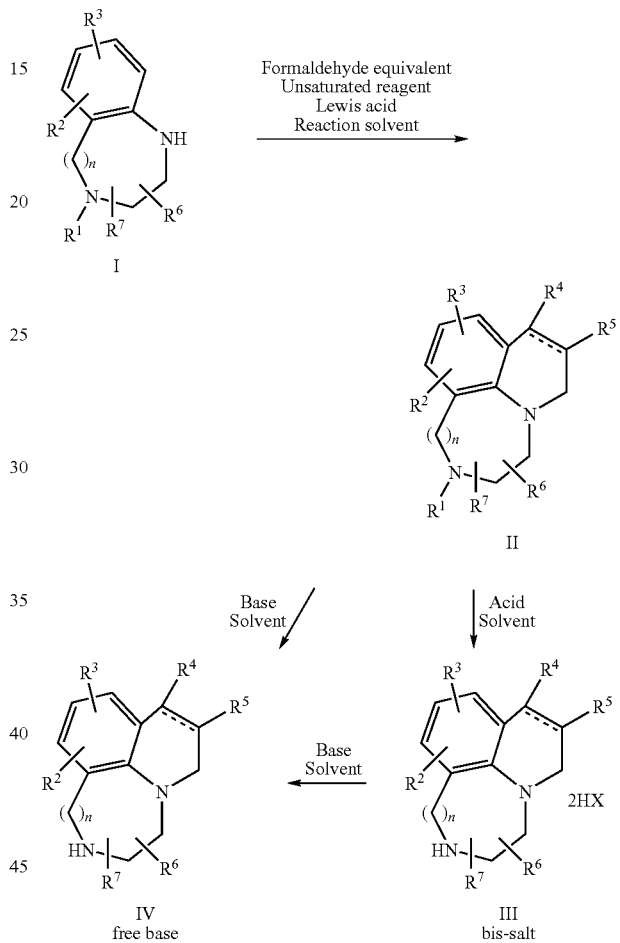

Compounds of formula II preferably are prepared by contacting a compound of formula I:

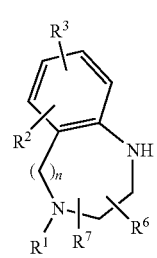

I wherein:
  $R^1$ is alkyl, alkanoyl, aroyl, carboalkoxy, or carboalkoxyaryl;

$R^2$ and $R^3$ are, independently, hydrogen, hydroxy, alkyl, alkoxy, halogen, carboxamido, carboalkoxy, perfluoroalkyl, cyano, alkanesulfonamido, alkanesulfonyl, alkanamido, amino, alkylamino, dialkylamino, perfluoroalkoxy, alkanoyloxy, alkanoyl, aroyl, aryl, arylalkyl, heteroaryl, or heteroarylalkyl;

$R^6$ and $R^7$ are, independently, hydrogen or alkyl; and n is 1 or 2, with a formaldehyde equivalent such as paraformaldehyde and an unsaturated reagent that preferably has the formula $R^4$—CH=CH—$R^5$ or formula $R^4$—C≡C—$R^5$ in the presence of a Lewis acid and a reaction solvent, and forming a compound of formula II:

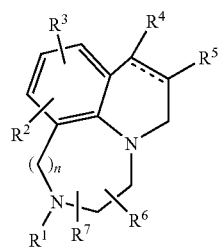

wherein:
$R^1$ is alkyl, alkanoyl, aroyl, carboalkoxy, or carboalkoxyaryl;

$R^2$ and $R^3$ are, independently, hydrogen, hydroxy, alkyl, alkoxy, halogen, carboxamido, carboalkoxy, perfluoroalkyl, cyano, alkanesulfonamido, alkanesulfonyl, alkanamido, amino, alkylamino, dialkylamino, perfluoroalkoxy, alkanoyloxy, alkanoyl, aroyl, aryl, arylalkyl, heteroaryl, or heteroarylalkyl;

$R^4$ and $R^5$ are, independently, hydrogen or alkyl or, taken together with the carbons to which they are attached, form a cyclic moiety that is cycloalkyl, cycloalkenyl, bridged bicyclic alkyl, bridged bicyclic alkenyl, pyranyl or thiopyranyl in which the sulfur atom is optionally oxidized to the sulfoxide or sulfone;

the dotted line represents an optional double bond.

$R^6$ and $R^7$ are, independently, hydrogen or alkyl; and n is 1 or 2.

Representative compounds according to the invention are those in which $R^1$ is alkyl, alkanoyl, aroyl, carboalkoxy, or carboalkoxyaryl. Preferred compounds are those in which $R^1$ is acetyl.

As defined generally above, $R^2$ and $R^3$ are each independently hydrogen, hydroxy, alkyl, alkoxy, halogen, carboxamido, carboalkoxy, perfluoroalkyl, cyano, alkanesulfonamido, alkanesulfonyl, alkanamido, amino, alkylamino, dialkylamino, perfluoroalkoxy, alkanoyloxy, alkanoyl, aroyl, aryl, arylalkyl, heteroaryl, or heteroarylalkyl. In preferred embodiments, both $R^2$ and $R^3$ are hydrogen.

As defined generally above, $R^4$ and $R^5$ are each independently hydrogen or alkyl of 1 to 6 carbon atoms, or, taken together with the carbons to which they are attached, form a cyclic moiety that is cycloalkyl, cycloalkenyl, bridged bicyclic alkyl, bridged bicyclic alkenyl, pyranyl or thiopyranyl in which the sulfur atom is optionally oxidized to the sulfoxide or sulfone. The dotted line represents an optional double bond. In preferred embodiments, the optional double bond is not present. In certain embodiments, $R^4$ and $R^5$ are taken together with the carbons to which they are attached to form a cycloalkyl ring. Cyclic groups formed by $R^4$ and $R^5$ are optionally substituted with one to three substituents independently selected from halogen, alkyl and alkoxy. Particularly preferred compounds are those in which $R^4$ and $R^5$, taken together with the carbons to which they are attached, form a cyclopentyl moiety.

$R^6$ and $R^7$ can, independently, be hydrogen or alkyl, with both preferably being hydrogen.

As defined generally above, n is 1 or 2, and in preferred embodiments is 1.

The compounds formed by the processes of this invention can contain asymmetric carbon atoms and thus give rise to optical isomers and diastereoisomers. While some formulas (such as, II, III, IV, etc.) herein are shown without respect to stereochemistry, the present invention includes all such optical isomers and diastereoisomers; as well as the racemic and resolved, enantiomerically pure R and S stereoisomers; as well as other mixtures of the R and S stereoisomers and pharmaceutically acceptable salts thereof.

Where an enantiomer is preferred, it may, in some embodiments be provided substantially free of the corresponding enantiomer. "Substantially free," as used herein, means that the compound is made up of a significantly greater proportion of one enantiomer. In preferred embodiments, at least about 95% by weight of a preferred enantiomer is present. In other embodiments of the invention, at least about 99% by weight of a preferred enantiomer is present. Preferred enantiomers may be isolated from racemic mixtures by any method known to those skilled in the art, including high performance liquid chromatography (HPLC) and chiral salt resolution, or prepared by methods described herein.

The term "diastereomeric salt" as used herein, is the adduct of a chiral amine such as:

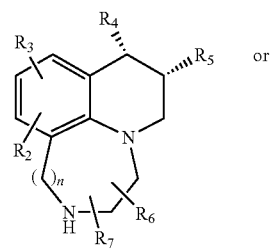

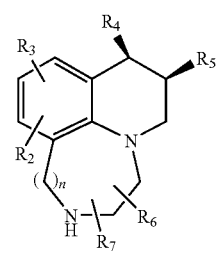

wherein each of $R^2$, $R^3$, $R^4$, $R^5$, $R^6$, $R^7$, and n is as defined above, with a chiral acid such as L-tartaric acid, and in the case of resolving chiral acids with two carboxyl groups includes both mono- and half-salts. The term "enantiomeric salt", as used herein refers to the salt of the resolved chiral amine such as:

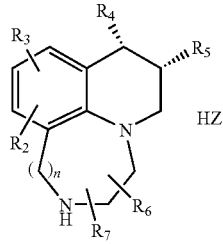

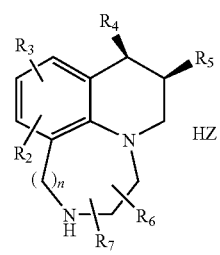

wherein each of $R^2$, $R^3$, $R^4$, $R^5$, $R^6$, $R^7$, and n is as defined above.

"Organic impurities" as used herein, refers to any organic by-product or residual material present in the desired product (such as those of formula IV or VI or salts thereof), and do not include residual solvents or water. "Total organic impurities" refer to the total amount of organic impurities present in the desired quinoline product. Percent organic impurities such as total organic impurities and single largest impurity, unless otherwise stated are expressed herein as HPLC area percent relative to the total area of the HPLC chromatogram. The HPLC area percent is reported at a wavelength where the desired product and maximum number of organic impurities absorb.

The term "alkyl," as used herein, refers to a hydrocarbon group having 1 to 8 carbon atoms, preferably 1 to 6 carbon atoms, and more preferably 1 to 4 carbon atoms. The term "alkyl" includes, but is not limited to, straight and branched groups such as methyl, ethyl, n-propyl, isopropyl, n-butyl, isobutyl, sec-butyl, t-butyl, n-pentyl, isopentyl, neo-pentyl, n-hexyl, and isohexyl. The term "lower alkyl" refers to an alkyl group having 1 to 4 carbon atoms.

Arylalkoxy, as used herein, refers to the group —O(CH$_2$)$_r$Ar, wherein r is 1-6.

Alkanamido, as used herein, refers to the group —NHC(O)R where R is an alkyl group.

Alkanoyl, as used herein, refers to the group —C(O)R where R is an alkyl group.

Alkanoyloxy, as used herein, refers to the group —OC(O)R where R is an alkyl group.

Alkanesulfonamido, as used herein, refers to the group —NHS(O)$_2$R where R is an alkyl group.

Alkanesulfonyl, as used herein, refers to the group —S(O)$_2$R where R is an alkyl group.

Alkoxy, as used herein, refers to the group —OR where R is an alkyl group.

The term "aryl" used alone or as part of a larger moiety as in "aralkyl", "aralkoxy", or "aryloxyalkyl", refers to monocyclic, bicyclic and tricyclic ring systems having a total of six to fourteen ring members, wherein at least one ring in the system is aromatic and wherein each ring in the system contains 3 to 7 ring members. The term "aryl" may be used interchangeably with the term "aryl ring".

The term "heteroaryl", used alone or as part of a larger moiety as in "heteroaralkyl" or "heteroarylalkoxy", refers to monocyclic ring systems having five to six ring members and 1-4 heteroatoms independently selected from nitrogen, oxygen, or sulfur. The term "heteroaryl" may be used interchangeably with the term "heteroaryl ring" or the term "heteroaromatic". In certain embodiments, such heteroaryl ring systems include furanyl, thienyl, pyrazolyl, imidazolyl, isoxazolyl, oxadiazolyl, oxazolyl, pyrrolyl, pyridyl, pyrimidyl, pyridazinyl, triazinyl, thiazolyl, triazolyl, and tetrazolyl, to name but a few.

Groups containing aryl or heteroaryl moieties may optionally be substituted with one to three substituents independently selected from halogen, alkyl, and alkoxy groups.

Aroyl, as used herein, refers to the group —C(O)Ar where Ar is aryl as defined above.

Arylalkyl, as used herein refers to the group —(CH$_2$)$_r$Ar where Ar is aryl as defined above and r is 1-6. Examples of arylalkyl groups include benzyl, phenethyl, 3-phenylpropyl, and 4-phenylbutyl.

Heteroarylalkyl, as used herein, refers to the group —(CH$_2$)$_r$Het, wherein Het is a heteroaryl group as defined above and r is 1-6.

Carboxamido, as used herein, refers to the group —C(O)NH$_2$.

Carboalkoxy, as used herein, refers to the group —C(O)OR where R is alkyl.

Carboalkoxyaryl as used herein, refers to the group —C(O)O(CH$_2$)$_r$Ar where Ar is aryl as defined above, and r is 1-3. Preferably, Ar is phenyl and r is 1 to form a benzyl moiety.

Halogen (or halo) as used herein refers to chlorine, bromine, fluorine and iodine.

Cycloalkyl and cycloalkenyl, as used herein, refer to saturated and partially unsaturated, respectively, monocyclic hydrocarbon rings containing 3 to 8 carbon atoms, and preferably containing rings of 5, 6, or 7 carbon atoms. In the case of cycloalkenyl, the hydrocarbon ring preferably contains one to two double bonds and more preferably one double bond.

Bridged bicyclic cycloalkyl and bridged bicyclic cycloalkenyl, as used herein, refer to saturated and partially unsaturated, respectively, bicyclic hydrocarbon rings containing 8 to 10 carbon atoms. "Bridged", as used herein, refers to there being at least one carbon-carbon bond between two non-adjacent carbon atoms of the hydrocarbon ring. In the case of bridged bicyclic cycloalkenyl, the hydrocarbon ring preferably contains one to two double bonds and more preferably one double bond.

The yield of the compound of formula II is preferably greater than about 60%; more preferably greater than about 75%; more preferably greater than about 85%; and still more preferably greater than about 91%. Yield, as used herein and unless indicated otherwise, refers to the yield from the immediate reaction rather than the overall synthesis.

Preferred compounds according to the invention are those in which n is 1. Particularly preferred compounds are those in which $R^1$ is acetyl or hydrogen, $R^2$, $R^3$, $R^6$ and $R^7$ are hydrogen, n is 1, and $R^4$ and $R^5$ are taken together with the carbons to which they are attached to form a cyclopentyl moiety.

Preferred cyclopentyl-containing compounds are those having stereochemistry exemplified by the salt of formula G:

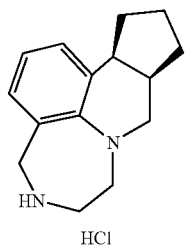

In some embodiments, the formaldehyde equivalent is added in solid form to the reaction solvent to form a reaction suspension or the solid formaldehyde equivalent may be suspended in a reaction solvent and added to the reaction mixture. In some preferred embodiments, paraformaldehyde is used as the formaldehyde equivalent, and is added in amounts sufficient to consume a compound of formula I. In some embodiments, paraformaldehyde is preferably added in amounts of at least about 0.90 mole equivalents, more preferably in amounts of about 0.90 mole equivalents to about 1.10 mole equivalents, and most preferably in amounts of from about 1.0 mole equivalents to about 1.05 mole equivalents relative to the starting compound of formula I.

Paraformaldehyde is preferably in a solid form. Paraformaldehyde suitable for the reaction is commercially available in prills (or other granulated forms) and powders from a variety of suppliers such as Aldrich, Fluka, Celanese Chemicals, J. T. Baker, Mallinckrodt Laboratory Chemicals, Miljac Inc., Sego Int. Corp., Spectrum Chemicals Mfg., Total Specialty Chemicals Inc., US Chemicals Inc., Riedel-de Haen, Acros Organics, Pfaltz & Bauer Chemicals, Derivados, Lancaster Synthesis and EM Science. Preferred powder forms have at least about 10% particles retained on a 200 mesh screen.

Lewis acids useful in the present invention are compounds that act as electron pair acceptors. Lewis acids useful in the present invention include those of the formula $TiX_4$, $ZrX_4$, $AlX_3$, $BX_3$, $SiX_4$, $SnX_2$, $SnX_2$, $R_yAlX_{(3-y)}$, $R_{(y)}SiX_{4-y}$, $R_yBX_{(3-y)}$ and combinations thereof, wherein X is a halogen, or —OR; R is an alkyl or aryl; and y is 0-3. $BF_3$ is particularly preferred. Preferably, the Lewis acid, such as $BF_3$, is used in amounts of about 2 mole equivalents to about 4 mole equivalents relative to the compound of formula I.

The unsaturated reagent used in forming the compound of formula II is preferably an alkene (including mono- and dienes) or alkyne. Preferred reagents include those of formula $R^4$—CH═CH—$R^5$ or formula $R^4$—C≡C—$R^5$. Cyclopentene is particularly preferred. The unsaturated moiety, such as cyclopentene, is preferably used in amounts of about 2 mole equivalents to about 8 mole equivalents relative to the compound of formula I.

Reaction solvents useful in this invention for forming a compound of formula II include polar aprotic solvents such as alkyl nitriles (e.g., acetonitrile, propionitrile and butyronitrile), alkyl esters (e.g., ethyl acetate), N-alkyl formamides (e.g., dimethyl formamide), and chlorinated hydrocarbons (e.g., methylene chloride). In some embodiments, a reaction solvent is chosen that is capable of suspending the solid formaldehyde equivalent. Acetonitrile-containing solvents are preferred. Reaction solvents containing nearly all acetonitrile are particularly preferred. Preferred solvents include those that contain at least about 90 weight percent acetonitrile, preferably at least about 95 weight percent acetonitrile, and still more preferably at least about 98 weight percent acetonitrile. The reaction solvent is preferably added in an amount sufficient to dissolve the compound of formula I. In some embodiments, solvent is added in concentrations of at least about 6 ml solvent per gram of the compound of formula I.

Particularly preferred reaction conditions for forming compounds of formula II include contacting a compound of formula I with about 2 mol. eq. to about 9 mol. eq. of cyclopentene and about 0.9 mol. eq. to about 1.2 mol. eq. paraformaldehyde (preferably prills) in the presence of about 2.0 mol. eq. to about 4.0 mol. eq. $BF_3$ and acetonitrile (using about 5 to about 20 ml per 1 g compound of formula I). In this embodiment, reaction solvents that contain at least about 90 weight percent acetonitrile, and preferably nearly all acetonitrile, are particularly preferred. The reaction temperature is preferably from about 20° C. to about 50° C., and more preferably from about 30° C. to about 45° C.

In accordance with Scheme I, the compounds of formula II can be converted, if desired, to free base compound of formula IV by contact with a base in the presence of a suitable solvent, or alternatively, by contact with an acid in the presence of a suitable solvent to form a bis-salt of formula III, followed by contact of the bis-salt with a base to form the free-base of formula IV.

Conversion of a compound of formula II to a bis salt of formula III according to the invention preferably is effected by contacting the compound of formula II with an acid having a pKa less than 1 in the presence of a solvent suitable for forming a bis salt of formula III, and at a temperature and time sufficient to form the bis salt. The acid is preferably added in an amount of at least about 2 mol. eq. and more preferably in an amount of at least about 2 mol. eq. to about 4 mol. eq. relative to the compound of formula II. Acids that may be used include, for example, hydrochloric acid, alkyl- and/or aryl-sulfonic acids, sulfuric acid, phosphoric acid, hydrobromic acid, hydroiodic acid, and combinations thereof. Preferred solvents suitable for bis-salt formation include protic solvents such as alkanols and polar aprotic solvents which are miscible with water, such as dioxan or glyme and combinations thereof. Further examples of protic solvents include acetic acid or $C_1$-$C_4$ alcohols. Preferred alcohols include ethanol, methanol, 2-propanol, or 1-butanol. The use of hydrochloric acid and denatured ethanol is particularly preferred.

Conversion of a compound of formula II to a bis salt of formula III is preferably carried out in about a 3:1 mixture of alcohol and concentrated aqueous acid, more preferably in about a 2:1 mixture of alcohol and concentrated aqueous acid, and still more preferably in about a 1:1 mixture of alcohol and concentrated aqueous acid (by volume or weight). In the latter case, ethyl acetate typically is added to increase recovery of the bis salt. In a preferred embodiment, the compound of formula II is contacted with concentrated hydrochloric acid in the presence of ethanol under reflux conditions for a time sufficient to form the bis salt of formula III. Bis salts of formula III are preferably formed in yields of about 80% and more preferably about 85%.

The bis salt of formula III can be contacted with base to form the corresponding free base compound of formula IV. Preferably the bis salt and base are combined in the presence of a suitable solvent in which the bis salt is at least partially soluble in such as hot (about 60° C. to 80° C.) water, polar solvents such as alkyl alcohols, such as $C_1$ to $C_4$ alcohols (e.g. ethanol, methanol, 2-propanol), dioxane, or THF (tetrahydrofuran) or combinations thereof to form the corresponding free base. The base is preferably added in an amount of at least about 2 mol. eq. and more preferably in an amount of at least about 2 mol. eq. to about 3 mol. eq. relative to the bis salt of formula III. Preferred bases include alkaline metal hydroxides or alkaline earth metal hydroxides, carbonates or phosphates, as well as organic bases and combinations thereof. Sodium hydroxide is preferred. The free base once formed may optionally be extracted using an extraction solvent. Preferred extraction solvents include solvents which are immiscible with water and have at least partial solubility with a compound of formula IV:

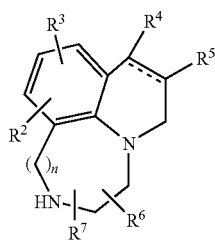

IV wherein each of $R^2$, $R^3$, $R^4$, $R^5$, $R^6$, $R^7$, and n is as defined herein.

Examples of such solvents include alkyl ethers, alkyl acetates, or aromatic hydrocarbons and combinations thereof such as tert-butylmethylether (TBME), diethyl ether, toluene, or ethyl acetate. The use of tert-butylmethylether is particularly preferred. Preferred methods for the preparation of the free base include adding sodium hydroxide solution (e.g., NaOH in water) to a hot suspension (70° C.-100° C.) of bis-HCl-salt in water to form the free base as an oil which can be separated by extraction with TBME.

Free bases of formula IV are prepared, for example, by contacting a compound of formula II with a suitable base, and preferably in the presence of a solvent suitable for free base formation. Preferred bases for this conversion are strong inorganic bases, i.e., those that completely dissociate in water under formation of hydroxide anion. The base is preferably added in an amount of at least about 1 mol. eq. and more preferably in an amount of at least about 1 mol. eq. to about 10 mol. eq. relative to the compound of formula II. Examples of such bases include alkaline metals, alkaline earth metal hydroxides, and combinations thereof. Potassium hydroxide is preferred. Examples of solvents suitable for use during free base formation include polar solvents such as alkyl alcohols, such as $C_1$ to $C_4$ alcohols (e.g. ethanol, methanol, 2-propanol), water, dioxane, or THF (tetrahydrofuran) or combinations thereof. Preferred solvents include $C_1$ to $C_4$ alcohols such as methanol, ethanol, 2-propanol, water and combinations thereof. The use of both potassium hydroxide and methanol is preferred. In preferred embodiments, the compound of formula II is refluxed in a mixture of methanol, water and potassium hydroxide in proportions of about 2 g methanol/1.5 g water/0.7 g potassium hydroxide per 1 g compound of formula II.

Alternatively, free bases of formula IV according to the invention can be prepared directly by contacting a compound of formula I, in which $R^2$, $R^3$, $R^6$ and $R^7$ are defined as before and $R^1$ is hydrogen, with a formaldehyde equivalent, such as paraformaldehyde, and a reagent having either formula $R^4$—CH=CH—$R^5$ or formula $R^4$—C≡C—$R^5$ in the presence of a Lewis acid and an alkyl nitrile containing solvent wherein the formaldehyde equivalent, reagent, Lewis acid and reaction solvent are as described above in connection with the formation of compounds of formula II. Preferably, the reaction conditions, including proportions of formaldehyde equivalent, unsaturated reagent, Lewis acid and reaction solvent relative to the compound of formula I are as described previously herein. In a more preferred embodiment, about 1.1 mole equivalents of paraformaldehyde, about 8 mole equivalents of cyclopentene, and about 3.5 mole equivalents of $BF_3$ relative to the compound of formula I are used to produce the free base compound of formula IV.

Generation of free base of formula IV from a bis salt of formula III typically provides higher yields for the subsequent formation of the diastereomeric salt than free base generated by direct hydrolysis with strong inorganic base. Additionally, formation of free base from a bis salt may typically be done without using highly caustic conditions.

Chiral free bases of formula IV, however formed, can be resolved by isolation or separation methods known in the art including, for example, high performance liquid chromatography and chiral salt resolution, or prepared by methods described herein.

In preferred embodiments, separation of enantiomers is achieved through contact of the free base of formula IV with a chiral resolving acid and a solvent for a time and under conditions to form the corresponding diastereomeric salt. Examples of useful chiral resolving acids include monofunctional carboxylic acid, difunctional carboxylic acid, sulfonic acid, phosphonic acid, and combinations thereof, that are relatively optically pure, i.e., at least about eight-five percent of a single enantiomer of the acid is present. Difunctional carboxylic acids include tartaric acid esters, such as diaroyl- (e.g., ditoluoyl-, dibenzoyl-,) diacetyl, di tert butyl-tartaric acid, and combinations thereof. Examples of such monofunctional carboxylic acids are mandelic acid and its oxygen-substituted derivates, and combinations thereof. Solvents preferred for use during resolution include polar protic and aprotic solvents that are capable of dissolving a compound of formula IV and the chiral acid and in which the desired diastereomeric salt has only limited solubility. Examples of such solvents include $C_2$-$C_4$ alcohols such as ethanol, isopropanol, n-propanol, n-butanol; ethyl acetate; isopropyl acetate; tetrahydrofuran; acetonitrile; and combinations thereof. Diastereomeric salts thus formed are preferably in yields of about 25%, more preferably about 30%, and still more preferably about 35% out of the maximum yield of 50%. (Maximum yield is 50% since only one enantiomer can be obtained.)

It is preferred that salt formation be accomplished using diaroyl tartaric acids such as ditoluoyl tartaric acid (DTTA). Preferred diastereomeric salts are those formed by contacting, in the presence of a solvent, ditoluoyl-L-tartaric acid with free base E:

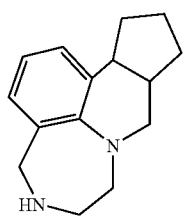

E to form diastereomeric salts having the formula F:

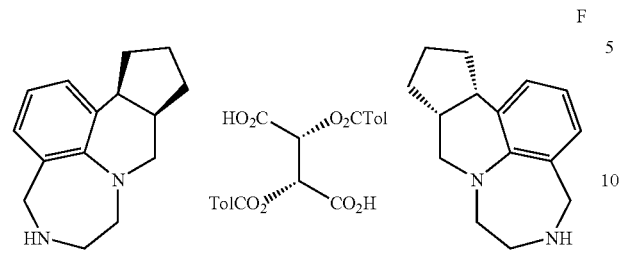

wherein Tol is a toluoyl group. The use of ditoluoyl tartaric acid and a solvent that contains isopropanol, ethyl acetate and combinations thereof is particularly preferred. In one embodiment, the chiral resolving acid is preferably contacted with the free base in an amount of about 0.2 mole equivalents to about 0.4 mole equivalents relative to the free base. In another embodiment, the reaction preferably includes using a solution having about 0.7 grams to about 1.3 grams of chiral resolving acid per about 10 ml solvent (such as isopropanol and/or ethyl acetate) that is added to a hot solution (temperature of about 70° C. to about 80° C.) having a concentration of about 4 ml to about 6 ml solvent (such as isopropanol) per gram of free base E.

The diastereomeric salt formed, such as diastereomeric salt F, is then isolated by methods known in the art. For example, the solution of chiral resolving acid and free base can be heated to near boiling, and then the resulting diastereomeric salt slowly cooled over a period of time to ambient temperature or cooler (if desired). After cooling, the solution is filtered to isolate the crystals. Such a procedure as to diastereomeric salt F typically results in crystals that are easily filterable. To increase purity, the resulting diastereomeric salt may optionally be resuspended in a solvent such as isopropanol, refluxed for a sufficient time (such as from about 1 hour to about 3 hours) and gradually cooled to recrystallize the salt.

Preferred yields of diastereomeric salts F are greater than about 25%, more preferably greater than about 30%, and still more preferably greater than about 35% (50% yield being maximum possible yield). The preferred chiral purity of the diastereomeric salt is greater than about 80 area percent HPLC, more preferably greater than about 85 area percent HPLC, and still more preferably greater than about 90 area percent HPLC relative to the total HPLC area of diastereomeric salts.

The resulting diastereomeric salt containing the desired enantiomer can be contacted, preferably in the presence of a solvent suitable for isolating the desired enantiomer, with an organic or inorganic acid having a pKa lower than the chiral resolving acid to form the desired resolved enantiomeric salt. Examples of such acids include hydrochloric acid, sulfuric acid, phosphoric acid, hydrobromic acid, hydroiodic acid, malic acid, succinic acid, trifluoro acetic acid, acetic acid, methane sulfonic acids, alkyl- and aryl-sulfonic acids and combinations thereof. Suitable solvents for forming the enantiomeric salt include polar solvents such as ethanol, methanol, isopropyl acetate, ethyl acetate, isopropanol, n-propanol, n-butanol, tetrahydrofuran, acetonitrile, and combinations thereof. Preferably, concentrated aqueous hydrochloric acid and ethyl acetate are employed.

In a preferred procedure a suspension of diastereomeric salt F in ethyl acetate and about 1 to about 1.5 molar equivalents hydrochloric acid (in concentrated aqueous form) relative to the diastereomeric salt is heated to reflux for about four hours to form the enantiomeric salt G:

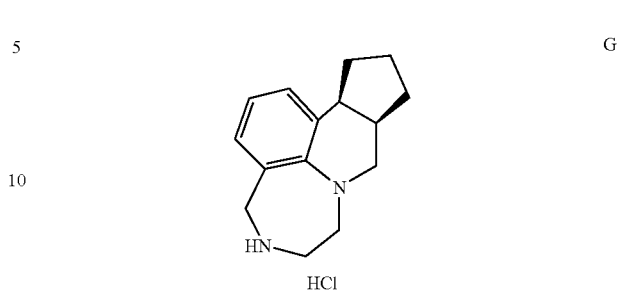

The resulting enantiomeric salt may be isolated by techniques known to those skilled in the art such as by crystallization followed by separation of the crystals. For example, in one preferred embodiment the resulting solution of enantiomeric salt may be cooled gradually to form crystals of the enantiomeric salt, followed by filtration to isolate the crystals. The isolated crystals may then optionally be recrystallized to increase purity. For example, in one preferred embodiment, the isolated crude enantiomeric salt is mixed in a suitable solvent and heated to dissolve the enantiomeric salt. The solution is then gradually cooled to effect crystallization. Examples of preferred solvents from which the enantiomeric salts are recrystallized include protic solvents such as $C_1$-$C_4$ alcohols including ethanol, methanol, isopropanol, n-propanol, n-butanol; water miscible polar aprotic solvents such as tetrahydrofuran, dioxan, acetone, acetonitrile; water; and combinations thereof. Preferably, the recrystallization solvent used is a $C_1$ to $C_4$ alcohol or mixtures of $C_1$ to $C_4$ alcohols with water.

In a preferred embodiment, crude enantiomeric salt G is dissolved in hot denatured ethanol (about 60° C. to about 75° C.), and water is then added in a ratio of 1 ml water per about 10 ml to 15 ml ethanol. The resulting solution is then cooled to about 5° C. over 3 hours. The resulting enantiomeric salt G is easily filterable and has needle shaped crystal morphology. The crystals may then be optionally reduced in particle size such as by milling and/or micronization. Preferably, the enantiomeric salt G is reduced in particle size to convert the needles to short rods preferably having an aspect ratio of less than about three. Such size reduction of the needle shaped particles facilitates powder flow during subsequent processing. Preferably after particle size reduction, the median (50%) particle size of enantiomeric salt G is less than about 25 microns, and 90% of the particles are preferably less than about 70 microns as measured by laser diffraction (such as by a Malvern particle size analyzer or equivalent).

A compound of formula G, however formed, is preferably present in at least about 90 area percent HPLC chiral purity, more preferably at least about 95 area percent HPLC chiral purity, and even more preferably at least about 99 area percent HPLC or 99.5 area percent HPLC chiral purity relative to the total HPLC area of stereoisomers. The preferred yields of the product through the foregoing route are about 60% more preferably about 70%, and still more preferably about 80%.

Although we do not wish to be bound by any particular theory, it is believed that conversion of a compound of formula I to a compound of formula II using a solid formaldehyde equivalent such as paraformaldehyde or trioxane that may gradually dissolve and/or breakdown into formaldehyde in the reaction solvent minimizes formation of the corresponding methylene dimer.

For example when solid formaldehyde equivalent such as paraformaldehyde or trioxane in acetonitrile is used, a composition comprising a compound of formula II and preferably no more than about 10 area percent HPLC (determined by the UV absorption at 220 nm) more preferably no more than about 5 area percent HPLC of the corresponding methylene dimer of formula VIII:

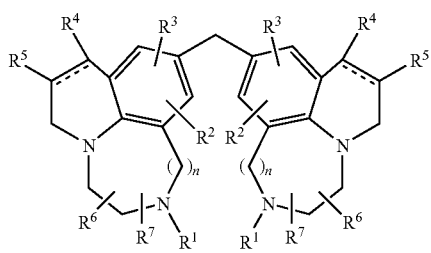

VII is formed (based on total area of HPLC chromatogram). When dimethoxy methane in acetonitrile is used about 50 area percent HPLC of the corresponding methylene dimer is formed. When aqueous formaldehyde solution was used dimer was formed to about 20 area percent HPLC and the starting compound of formula I was degraded. Powdered paraformaldehyde is generally preferred, particularly when used in high dilution (20 ml acetonitrile per 1 g compound of formula I) Trioxane gave similar results to the paraformaldehyde prills but typically with extended reaction times. Using paraformaldehyde prills lead to about 4 area percent HPLC of methylene dimer formation.

To the extent that the reaction product of this conversion is carried forward in the synthetic scheme, the formation of dimeric forms of the corresponding bis salts, free bases, diastereomeric salts, and enantiomeric salts is minimized, as well. The present invention preferably provides the compounds of formula II and all reaction products derived from them as compositions comprising the compounds of formula II or derivative thereof and less than about 10 area percent HPLC, more preferably less than about 7 area percent HPLC and even more preferably less than about 5 area percent HPLC of the corresponding methylene dimer, (based on total area of HPLC chromatogram). Thus, the invention provides compositions comprising the compounds of formula II and less than about 10 area percent HPLC of their corresponding methylene dimers, compositions comprising the bis salts of formula III and less than about 10 area percent HPLC of their corresponding methylene dimers, compositions comprising the free bases of formula IV and less than about 10 area percent HPLC of their corresponding methylene dimers, compositions comprising the diastereomeric salts of the invention and less than about 10 area percent HPLC of their corresponding methylene dimers, and compositions comprising the enantiomeric salts of the invention and less than about 10 area percent HPLC of their corresponding methylene dimers, (based on total area of HPLC chromatogram).

In a preferred embodiment, the process of the present invention provides a composition containing enantiomeric salt G. In some embodiments the composition contains enantiomeric salt G in an amount of at least about 96.5 weight percent and more preferably at least about 98 weight percent on an anhydrous basis, based on the total weight of the composition.

In some other embodiments, the composition containing enantiomeric salt G preferably contains from about 12.8 weight percent to about 14.8 weight percent, and more preferably from about 13.5 weight percent to about 14.5 weight percent HCl from G as measured by ion chromatography based on the total weight of the composition.

In other embodiments, the composition containing enantiomeric salt G preferably contains no more than about 2.0 area percent HPLC of total organic impurities and more preferably no more than about 1.5 area percent HPLC total organic impurities relative to the total area of the HPLC chromatogram. In other embodiments, the composition containing enantiomeric salt G preferably contains no more than about 0.6 area percent HPLC of any single impurity such as the corresponding methylene dimer and more preferably no more than about 0.5 area percent HPLC of any single impurity relative to the total area of the HPLC chromatogram. According to another embodiment, the composition containing enantiomeric salt G preferably contains no more than about 0.2 area percent HPLC of any single impurity relative to the total area of the HPLC chromatogram. According to yet another embodiment, the composition containing enantiomeric salt G preferably contains no more than about 0.2 area percent HPLC of total impurities relative to the total area of the HPLC chromatogram.

In yet other embodiments of the present invention, the composition containing enantiomeric salt G preferably contains no more than about 2.0 weight percent water and more preferably no more than about 0.30 weight percent water as measured by Karl Fischer titration based on the total weight of the composition.

In other embodiments, the composition contains G at least one residual solvent in an amount of about 0.5 weight percent or less. Other embodiments provide compositions containing Compound G and at least one organic impurity or residual solvent selected from at least one of ethanol, ethyl acetate, isopropanol, methanol, or a dimer compound of formula H:

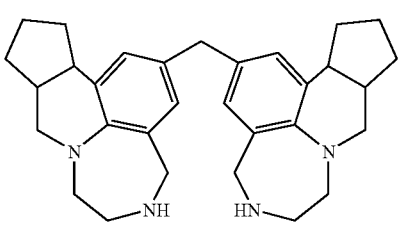

H or a salt thereof. In yet other embodiments of the invention, the composition containing enantiomeric salt G preferably contains no more than about the following residual solvents individually alone or in any combination: 0.5 weight percent ethanol, 0.5 weight percent methanol, 0.5 weight percent ethyl acetate, 0.5 weight percent isopropanol and/or 0.5 weight percent t-butyl methyl ether based on the total weight of the composition.

One representative synthesis of compounds having formula G is shown in the following synthetic scheme and discussed in greater detail in the experimental examples that follow:

Scheme 2

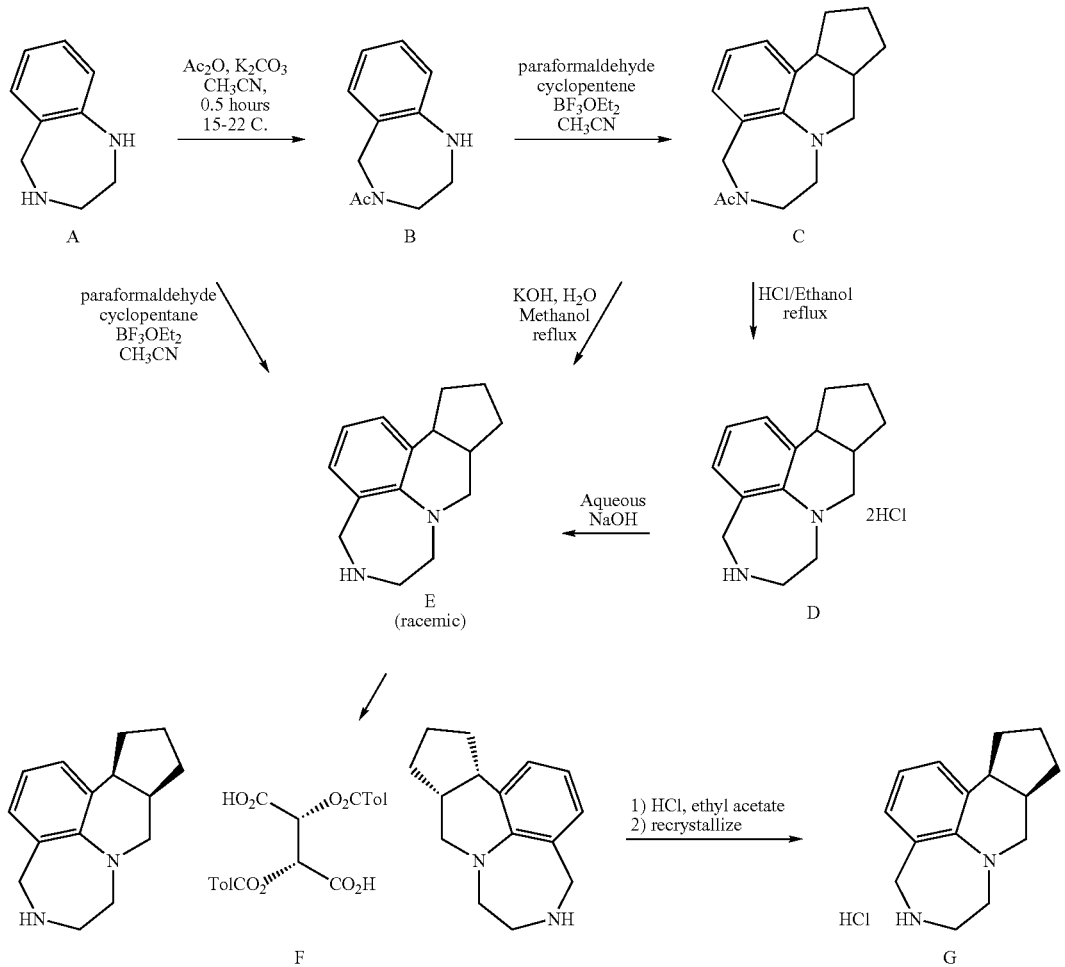

The preferred overall yield of syntheses of this type is greater than about 10%, more preferably greater than about 15%, and still more preferably greater than about 20%.

The present invention also relates to compounds of formula IX and methods for preparing them. Such compounds of formula IX are useful, for example, for synthesis of psychotic and anti-obesity agents. In preferred embodiments, compounds of formula IX are prepared by contacting compound of formula VIII:

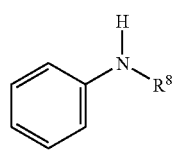

VIII with an unsaturated reagent having formula $R^4$—CH=CH—$R^5$ or $R^4$—C≡C—$R^5$ in the presence of a Lewis acid, a formaldehyde equivalent and a reaction solvent, thereby forming a compound of formula IX:

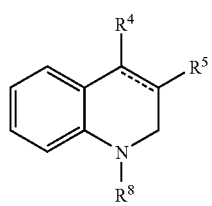

IX where the formaldehyde equivalent is preferably in solid form at least prior to the contacting.

Representative compounds according to the invention are those in which $R^4$ and $R^5$ are, independently, hydrogen or alkyl of 1 to 6 carbon atoms or, taken together with the carbons to which they are attached, form a cyclic moiety that is cycloalkyl, cycloalkenyl, bridged bicyclic alkyl, bridged bicyclic alkenyl, pyranyl or thiopyranyl in which the sulfur atom is optionally oxidized to the sulfoxide or sulfone. Cyclic groups formed by $R^4$ and $R^5$ may optionally be substituted with one to three substituents independently selected from halogen, alkyl, or alkoxy. Particularly preferred compounds are those in which $R^4$ and $R^5$, taken together with the carbons to which they are attached, form a cyclopentyl moiety.

$R^8$ is a branched or straight chain alkyl group such as methyl, ethyl, n-propyl, isopropyl, butyl, or tertiary butyl; a hetero-substituted alkyl group such as a protected ethylamino or ethoxy group; an aryl; or an arylalkyl group. In preferred embodiments, $R^8$ is either methyl or benzyl.

Lewis acids useful for preparing compounds of formula IX include those that are capable of depolymerizing formaldehyde equivalents and those that facilitate the anilinium ion formation. Suitable acids include those previously mentioned, for example, those of formula $TiX_4$, $ZrX_4$, $AlX_3$, $BX_3$, $SiX_4$, $SnX_2$, $SnX_2$, $R_yAlX_{(3-y)}$, $R_{(y)}SiX_{4-y}$, $R_yBX_{(3-y)}$, where X is a halogen or —OR; R is an alkyl or aryl; and y is 0-3, and combinations thereof. Boron trifluoride is particularly preferred.

Formaldehyde equivalents suitable for forming compounds of formula IX include those previously described such as paraformaldehyde (including prills and powders), dimethoxymethane, formalin, trioxane, and poly and oligomeric forms of formaldehyde in general as well as solutions of formaldehyde. Formaldehyde equivalents that are provided to the reaction in solid form such as paraformaldehyde and trioxane are particularly preferred. A preferred unsaturated reagent for use in the present invention is cyclopentene.

Solvents useful in preparing compounds of formula IX include polar aprotic solvents such as alkyl nitriles (e.g., acetonitrile, propionitrile and butyronitrile), esters (e.g., ethyl acetate), N-alkyl formamides (e.g., dimethyl formamide), chlorinated hydrocarbons (e.g., methylene chloride), and mixtures thereof. Alkyl nitrile-containing solvents are preferred. Solvents containing nearly all acetonitrile are particularly preferred. Preferred solvents include those that contain at least about 90 weight percent alkyl nitrile, preferably at least about 95 weight percent alkyl nitrile, and still more preferably at least about 98 weight percent alkyl nitrile.

The solvent preferably is added in an amount sufficient to dissolve starting material. In some embodiments, solvent is added in concentrations of at least about 6 ml solvent per gram starting compound of formula VIII. The combination of boron trifluoride, paraformaldehyde and acetonitrile is particularly preferred. Reaction at temperatures between about 1° C. to about 30° C. are preferred. Relative to the compound of formula VIII, in a preferred embodiment, the reaction to form compounds of formula IX, employs from about 2 to about 4 mole equivalents $BF_3$, from about 2 to about 9 mole equivalents cyclopentene, and from about 0.9 to about 1.1 equivalents paraformaldehyde (prills) in acetonitrile (using about 10 ml to about 20 ml per 1 g starting material) are particularly preferred.

Compounds of formula IX preferably are formed in yields of at least about 55%. In preferred embodiments compounds of formula IX are formed in yields greater than about 60%, more preferably yields greater than about 70%, even more preferably yields greater than 80%, and still more preferably yields greater than about 90%.

The invention is further demonstrated in the following examples. The examples are for purposes of illustration and are not intended to limit the scope of the present invention.

EXAMPLES

Example 1

4-Acetyl-2,3,4,5-tetrahydro-1H-1,4-benzodiazepine (B)

To a 10 L jacketed reactor equipped with an overhead stirrer, thermocouple, condenser, and positive nitrogen pressure, was charged 6.8 L acetonitrile, 430.0 g (2.90 mol) compound A (1,4-benzodiazepine) and 441.0 g (3.19 mol, 1.1 eq) potassium carbonate. The stirred mixture was cooled to 0° C. Acetic anhydride (311.4 g, 3.05 mol, 1.05 eq) was added dropwise to the reaction mixture over a period of 30 minutes. The reaction was monitored by HPLC showing no more than 2% of compound A after 30 minutes. The reaction was quenched by addition of butylamine (21.2 g, 0.29 mol, 0.1 eq) and the inorganic solids were removed by filtration.

The cake was washed with 1.1 L acetonitrile. The filtrate was concentrated to a volume of 0.95 L by vacuum distillation (42-55° C., 177-190 mmHg) and toluene (2.1 L) was added to the concentrate. The mixture was again concentrated to a volume of 1.20 L by vacuum distillation and toluene (0.52 L) was added. The reaction mixture was cooled to 35° C. and seeds (200 mg of compound B) were added. Heptane (1.72 L) was added at 20° C. and the mixture was cooled to 0° C. for 1 h and to −5° C. for 0.5 h.

The solid product compound B was collected by filtration and the cake was washed twice with 0.55 L of heptane. The yellow solid was dried for 24 hours under vacuum at 40° C. to give 515.5 g compound B, (93% of theoretical). $^1$H NMR (300 MHz, DMSO-d6): δ=2.00 (s, 1.2H), 2.1 (s, 1.8H), 3.02-3.13 (m, 2H), 3.58-3.62 (m, 2H), 4.40 (s, 0.4H), 4.56 (s, 0.6H), 5.59 (s, 0.4H), 5.65 (s, 0.6H) 6.67-6.82 (m, 2H), 7.00-7.16 (m, 2H) ppm.

Example 2

5-Acetyl-4,5,6,7,9,9a,10,11,12,12a-decahydrocyclopenta[c][1,4]diazepino[6,7,1-ij]quinoline] (C)

To a 1.0 L jacketed reactor equipped with an overhead stirrer, thermocouple, condenser, addition funnel and positive nitrogen pressure was charged acetylbenzodiazepine (40.0 g, 210 mmol, 1.0 eq.), paraformaldehyde prills (6.30 g, 210 mmol, 1.0 eq.), acetonitrile (480 ml) and cyclopentene (86.0 g, 1.26 mol, 6.0 eq.). To the reaction suspension at 12° C. was added boron trifluoride etherate (80.5 g, 567 mmol, 2.7 eq.) in 20 minutes. The reaction mixture was heated. The reaction was monitored by HPLC. After the completion of the reaction, aqueous sodium hydroxide solution (50.0 g NaOH in 250 ml of water) was added. The resulting mixture was filtered, the top organic layer was washed with brine (50.0 ml). The organic layer was concentrated to 133 ml. Water (160 ml) was added to the hot concentrated mixture. The reaction mixture was cooled to ambient temperature and filtered. The cake was washed with a mixture of water and acetonitrile (5:1, 60 ml, 2 times). The wet product (82.0 g) was dried in a vacuum oven for 20 h at 45° C. to afford compound C (52.8 g, yield 93%) as an off-white solid. HPLC (area %): 94.5% C, 3.15% dimeric impurity compound methylene bis[(±)-4,5,6, 7,9,9a,10,11,12,12a-decahydrocydopenta[c][1,4]diazepino [6,7,1-ij]quinoline] $^1$H NMR (300 MHz, DMSO-d6): δ=7.17-6.94 (m, 2H), 6.85-6.73 (m, 1H), 4.81 (d, j=13.7 Hz, 0.4H), 4.56 (d, j=15.3 Hz, 0.6H), 4.35 (d, j=15.3 Hz, 0.6H), 4.16 (m, 0.6H), 3.98 (d, j=13.7 Hz, 0.4H), 3.73 (m, 0.4H), 3.49 (m, 0.4H), 3.30-2.81 (m, 4.6H), 2.63 (m, 1H), 2.21 (m, 2H), 1.98 (m, 4H), 1.57 (m, 2H), 1.27 (m, 2H) ppm. (two conformers at 25° C.) dimeric impurity compound methylene bis[(±)-4,5,6,7,9,9a,10,11,12,12a-decahydrocyclopenta[c] [1,4]diazepino[6,7,1-ij]quinoline]: δ=7.08-6.77 (m, 4H), 4.95 (m, 0.6H), 4.39 (m, 4H), 4.05 (m, 0.4H), 3.29-267 (m, 3H), 2.33-1.93 (m, 15H), 1.76-1.20 (m, 6H) ppm. LC/MS: (552 m/z)

Example 3

(−)-4,5,6,7,9,9a,10,11,12,12a-Decahydrocyclopenta [c][1,4]diazepino[6,7,1-ij]quinoline (R,R)-di-p-toluoyltartaric acid salt (F) by alkaline hydrolysis To a (2 L) jacketed reactor equipped with an overhead stirrer, thermocouple, condenser, and positive nitrogen pressure was charged methanol (500 ml), water (140 ml) and the mixture was cooled to 5±5° C. Potassium hydroxide pellets (284.7 g, 2.263 mol) were added in 34 portions. The reaction mixture was warmed to 35±5° C. and compound C (Scheme 2, 195.4 g, 0.650 mol) was added. The suspension was refluxed for 18 hours. After cooling the reaction mixture to 0° C., water (385.0 g) followed by concentrated hydrochloric acid (325.0 g, 3.25 mol. 5.0 eq) was added to the reaction mixture. Ethyl acetate (600 ml) was added and the mixture was stirred for 15 minutes and filtered. The cake was washed with ethyl acetate (1400 ml), the washes were kept separate from mother liqueur. The filtrate layers were split and the aqueous layer was extracted with washes from the filtrate. The combined organic layers were concentrated to a volume of 450 ml. Ethyl acetate (850 ml) was added to the mixture. The solution was concentrated to a volume of 300 ml. The concentrate was distilled twice azeotropically with isopropanol (750 ml). Isopropanol (700 ml) was charged to the residue and the mixture was heated to 70° C. The hazy solution was clarified by filtration over celite (16 g), and washed with Isopropanol (100 ml). The solution of E (racemic) was heated to 70° C. and a solution of di-p-toluoyl-L-tartaric acid (DTTA) (75.4 g, 0.165 mol, 0.30 eq) in isopropanol (600 ml) was added maintaining the internal temperature above 70° C.

Seeds were added and the reaction mixture was allowed to cool to 20±5° C. over a period of 3 hours. The solid F formed was collected by filtration (filtration time=15 min, cake: height=2.0 cm, diameter=11.5 cm). The wet crude F (89.1 g) (87% chiral purity) was suspended in isopropanol (630 ml) and heated to reflux for 2 hours. The mixture was allowed to cool to room temperature, the solid was collected by filtration and washed with isopropanol (155 ml). After drying at 40° C. for twelve hours, F (65.8 g, 24% yield, of the theoretical yield of 50%) was obtained with 92% chiral purity. $^1$H NMR (300 MHz, DMSO-d$_6$): δ=7.86 (d, j=8.0 Hz, 4H), 7.32 (d, j=8.0 Hz, 4H), 7.14 (d, j=6.6 Hz, 2H), 6.81 (dd, j=6.3, 7.3 Hz, 2H), 5.57 (s, 2H), 3.90 (dd, j=13.8, 36.2 Hz, 4H), 3.15 (m, 2H), 3.02-2.87 (m, 10H), 2.59 (t, j=12.5 Hz, 2H), 2.37 (s, 6H), 2.19-2.15 (m, 4H), 1.99-1.96 (m, 2H), 1.62-1.58 (m, 4H), 1.35-1.21 (m, 4H) ppm. Chiral HPLC: chirobiotic V 3.9×150 mm 5 μm, eluent 1 L Methanol/0.9 g NH$_4$CF$_3$CO$_2$, flow: 1.5 ml, detect. 220 nm UV, Retention Time: E(S)=4.71 min, E(R)=4.38 min.

Example 4

(−)-4,5,6,7,9,9a,10,11,12,12a-Decahydrocyclopenta [c][[1,4]diazepino[6,7,1-ij]quinoline (R,R)-di-p-toluoyltartaric acid salt (F) by acidic hydrolysis Compound C (0.30 kg, 1.1 mol) was added to a 5-10° C. mixture of concentrated HCl (2.5 eq, 0.274 kg, 2.77 moles) and ethanol (0.30 L, 0.23 kg). The suspension was refluxed for 12-15 hours and reaction completion was monitored by HPLC. After the reaction was complete, ethyl acetate was added (0.802 kg, 0.90 L) over 40 minutes. The reaction mixture was cooled to ambient temperature, filtered and washed with ethyl acetate (0.40 L, 0.356 kg) to afford the di-hydrochloride salt D (0.291 g, 87%). $^1$H NMR (300 MHz, DMSO-d6): δ=10.12 (m, 2H), 9.05 (m, 1H), 7.24 (d, j=7.23 Hz, 1H), 7.18 (d, j=6.4 Hz, 1H), 6.92 (dd, j=6.4, 7.3 Hz, 1H), 4.13 (m, 2H), 3.44 (m, 1H), 3.09 (m, 4H), 2.93 (m, 1H), 2.67 (t, j=12.6 Hz, 1H), 2.24 (m, 2H), 2.01 (m, 1H), 1.61 (m, 2H), 1.33 (m, 2H) ppm. Anal. Calculated for C$_{15}$H$_2$Cl$_2$N$_2$: C, 59.80; H, 7.36; Cl, 23.54; N, 9.30. Found: C, 59.82; H, 7.70; Cl, 23.42; N, 9.39.

D was heated to 75±5° C. in water (0.870 L, 0.874 kg) to give a solution. The free base was generated in aqueous NaOH (0.249 kg 50/50 w/w sodium hydroxide solution in 0.119 kg water) and was cooled to 35±5° C. in 1 hour before it was extracted with TBME (0.450 L, 0.329 kg). After a solvent exchange to isopropanol (0.92 L, 0.710 kg), the organic layer was concentrated to (0.5 L, 0.459 kg). Isopropanol (0.920 L, 0.710 kg) was added to the concentrated mixture. Di-p-toluoyl-L-tartaric acid (DTTA) (0.23 eq, 0.101 kg, 0.26 mols) in ethyl acetate (1.20 L, 1.02 kg) solution was added dropwise to the free base solution in 1 hour at 75±5° C. The solution was cooled to ambient temperature in 6 hours. The product was filtered and washed with ethyl acetate (0.400 L, 0.352 kg). Finally, the crude F was re-slurried in IPA (0.86 L, 0.667 kg) at reflux for 2 hours and then cooled to ambient temperature for 4 hours. The product was filtered and washed with IPA (0.153 kg, 0.2 L). The wet product (223.7 g) was dried in a vacuum oven for 24 hours at 40° C. to afford F (150.7 g, 32.3% yield from C). HPLC: 98.77%, Chiral Purity: 90%.

Example 5

(−)-4,5,6,7,9,9a,10,11,12,12a-Decahydrocyclopenta [c][1,4]diazepino[6,7,1-ij]quinoline hydrochloride (G)

To a suspension of F (72.0 g, 171 mmol) in ethyl acetate (860 ml) in a 2.0 L flask, was added concentrated HCl (20.0 g, 205 mmol, 1.2 eq.) at ambient temperature. The suspension was refluxed for 3 hours and cooled to ambient temperature. It was filtered and washed with ethyl acetate (115 ml) to afford the crude hydrochloride salt (46.0 g, G). The latter was heated to 70° C. in ethanol (276 ml, 200 proof, denatured with 4% ethyl acetate) and then water (22 ml) was added. The solution was cooled to 5° C. over 3 hours. The product was filtered and washed with ethanol (46 ml). The wet product (34.6 g) was dried in a vacuum oven for 20 hours at 40° C. to afford G (32.0 g, yield 70%) as an off-white solid. HPLC (area %): 99.45% Chiral purity (HPLC): 99.9%

Analysis of separate batches of G prepared according to the procedures of Examples 1, 2, 4, and 5 are described in the following table:

with ethyl acetate (3 times, 10 ml). The combined organic layers were washed with brine and dried over MgSO$_4$. Evaporation of solvent and flash-chromatography with heptane/

| Tests | Batch 1 | Batch 2 | Batch 3 | Batch 4 |
|---|---|---|---|---|
| Purity (HPLC) (area %) | | | | |
| A) Total Organic Impurities | 0.29% | 0.43% | 1.48% | 0.51% |
| B) Largest Single Impurity | 0.11%[a] | 0.21%[a] | 0.58% [RRT = 3.31][b] | 0.26% [RRT = 3.31][b] |
| HCl Content (weight %) (Ion Chrom.) | 14.1% | 14.0% | 13.8% | 14.0% |
| Water Content (wt %, KF) | 0.26% | 0.10% | 0.11% | 0.12% |
| Chiral Purity (area %) (HPLC) | Not tested | Not tested | 0.06% Enantiomer | 0.12% Enantiomer |
| Residual Solvents (wt %) (GC) | | | | |
| Acetonitrile | ND, DL = 5 | ND, DL = 8 ppm | ND, DL = 7 ppm | ND DL = 2 ppm |
| Cyclopentene | Not tested | Not tested | ND, DL = 0.0005% | ND, DL = 0.0001% |
| Ethanol | 0.06% | 0.18% | 0.48% | 0.21% |
| Ethyl Acetate | 0.001% | ND, DL = 0.0010% | 0.01% | 0.002% |
| Isopropanol | ND, DL = 0.00 | ND, DL = 0.0061% | ND, DL = 0.0032% | ND, DL = 0.0010% |
| t-Butyl methyl ether | Not Tested | Not Tested | Not Tested | ND, DL = 0.0003% |

ND = None detected.
DL = Detection limit.
NMT = Not more than.
RRT = Relative retention time.
[a]Purity was tested by a preliminary development method.
[b]Actual RRT = 3.22 (Variation due to HPLC gradient).

Example 6

(±)-4,5,6,7,9,9a,10,11,12,12a-Decahydrocyclopenta [c][1,4]diazepino[6,7,1-ij]quinoline BF$_3$.OEt$_2$ (2.2 ml, 17.5 mmol) was dropped to a mixture of benzodiazepine (0.74 g, 5 mmol), cyclopentene (3.6 ml, 40.0 mmol), paraformaldehyde (165 mg, 5.5 mmol) in acetonitrile (20 ml) at room temperature. The mixture was heated at 45° C. (oil bath) for 5 h. It was concentrated in vacuo. The residue was taken up with EtOAc (150 ml) and washed first with a mixture of aqueous Na$_2$CO$_3$ and NaOH (200 ml), and then with brine (200 ml). The organic layer was dried and added HCl (1 N in diethyl ether, 10 ml) and the resultant precipitates were collected by filtration. The mixture was purified by flash chromatography on silica gel (5-15% MeOH in CH$_2$Cl$_2$) to afford E (0.70 g, 53% yield.)

Example 7

5-Benzyl-2,3,3a,4,5,9b-hexahydro-1H-cyclopenta[c] quinoline

N-Phenyl-benzyl amine (4.58 g, 25.00 mmol) was dissolved in 57 ml acetonitrile under N$_2$ atmosphere. Cyclopentene (10.22 g, 150.0 mmol) and paraformaldehyde (788 mg, 26.25 mmol) were added in one portion. The mixture was cooled to 1.5° C. and BF$_3$.OEt$_2$ (8.87 g, 62.50 mmol) was added over a period of 2 minutes. The cooling bath was removed after addition was completed (reaction temp=9° C.). The reaction was completed after 2 hours (HPLC).

NaOH (10.5 g in 20 ml water) was added and the mixture stirred overnight. Layers were separated. An inorganic solid was separated by filtration and the organic layer was extracted with ethyl acetate (3 times, 10 ml). The combined organic layers were washed with brine and dried over MgSO$_4$. Evaporation of solvent and flash-chromatography with heptane/ethyl acetate gave 5-Benzyl-2,3,3a,4,5,9b-hexahydro-1H-cyclopenta[c]quinoline (5.97 g, 91% yield).

$^1$H NMR (300 MHz, DMSO-d6): δ=7.51-7.19 (m, 5H), 7.05 (d, j=7.4 Hz, 1H), 6.88 (t, j=7.4 Hz, 1H), 6.57-6.52 (m, 2H), 4.50 (dd, j=16.5, 24.2 Hz, 2H), 3.09 (dd, j=5.0, 11.7 Hz, 1H), 2.98-284 (m, 2H), 2.33 (m, 1H), 2.14 (m, 1H), 1.94 (m, 1H), 1.63-1.40 (m, 4H) ppm.

LC-MS: (263 m/z)

Example 8

5-Methyl-2,3,3a,4,5,9b-hexahydro-1H-cyclopenta[c] quinoline

N-methyl aniline (1.07 g, 10.0 mmol) was dissolved in 23 ml acetonitrile under N$_2$ atmosphere. Cyclopentene (4.08 g, 60.0 mmol) and paraformaldehyde (300 mg, 10.0 mmol) were added in one portion. The mixture was cooled to 1.5° C. and BF$_3$.OEt$_2$ (3.55 g, 25.0 mmol) was added over a period of 2 minutes. The cooling bath was removed after addition was completed (reaction temp=9° C.). The reaction was completed after 2 hours (HPLC). NaOH (10.5 g in 20 ml water) was added and the mixture stirred overnight. Layers were separated. An inorganic solid was separated by filtration and the organic layer was extracted with ethyl acetate 3×10 ml. The combined organic layers were washed with brine and dried over MgSO$_4$. Evaporation of solvent and flash-chromatography with heptane/ethyl acetate gave 5-Methyl-2,3,3a,4,5,9b-hexahydro-1H-cyclopenta[c]quinoline (1.08 g, 57% yield).

$^1$H NMR (300 MHz, DMSO-d6): δ=7.04-6.96 (m, 2H), 6.63-6.58 (m, 2H), 2.98-2.78 (m, 2H), 2.63 (t, j=9.93 Hz, 1H), 2.33 (m, 1H), 2.13 (9m, 1H), 1.93 (m, 1H), 1.60-1.34 (m, 4H) ppm.

LC-MS: (187 m/z)

We claim:
1. A method comprising the steps of:
a) providing a compound of formula I:

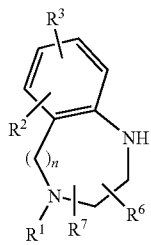

wherein:
$R^1$ is alkyl, alkanoyl, aroyl, carboalkoxy, or carboalkoxyaryl;
$R^2$ and $R^3$ are, independently, hydrogen, hydroxy, alkyl, alkoxy, halogen, carboxamido, carboalkoxy, perfluoroalkyl, cyano, alkanesulfonamido, alkanesulfonyl, alkanamido, amino, alkylamino, dialkylamino, perfluoroalkoxy, alkanoyloxy, alkanoyl, aroyl, aryl, arylalkyl, heteroaryl, or heteroarylalkyl;
$R^6$ and $R^7$ are, independently, hydrogen or alkyl;
n is 1; and
b) contacting the compound of formula I with at least one formaldehyde equivalent and a reagent having either formula $R^4$—CH=CH—$R^5$ or formula $R^4$—C≡C—$R^5$, in the presence of a Lewis acid and a reaction solvent to form a compound of formula II:

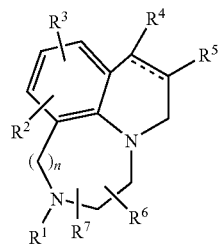

wherein the formaldehyde equivalent is in solid form at least prior to the contacting,
$R^1$ is alkyl, alkanoyl, aroyl, carboalkoxy, or carboalkoxyaryl;
$R^2$ and $R^3$ are, independently, hydrogen, hydroxy, alkyl, alkoxy, halogen, carboxamido, carboalkoxy, perfluoroalkyl, cyano, alkanesulfonamido, alkanesulfonyl, alkanamido, amino, alkylamino, dialkylamino, perfluoroalkoxy, alkanoyloxy, alkanoyl, aroyl, aryl, arylalkyl, heteroaryl, or heteroarylalkyl;
$R^6$ and $R^7$ are, independently, hydrogen or alkyl;
n is 1;
$R^4$ and $R^5$ are taken together with the carbons to which they are attached, form a cyclic moiety that is cycloalkyl, cycloalkenyl, bridged bicyclic alkyl, bridged bicyclic alkenyl, pyranyl or thiopyranyl in which the sulfur atom is optionally oxidized to the sulfoxide or sulfone; and
the dotted line represents an optional double bond.
2. The method of claim 1 wherein the formaldehyde equivalent comprises paraformaldehyde.
3. The method of claim 1 wherein the reaction solvent comprises an alkyl nitrile.
4. The method of claim 1 wherein:
$R^1$ is acetyl;
$R^2$, $R^3$, $R^6$ and $R^7$ are hydrogen;
n is 1;

$R^4$ and $R^5$, taken together with the carbons to which they are attached, form a cyclopentyl moiety;
the formaldehyde equivalent is paraformaldehyde; and
the reaction solvent comprises at least about 90 weight percent acetonitrile.
5. The method of claim 1 wherein the yield of the compound of formula II is greater than about 60%.
6. The method of claim 1 further comprising contacting the compound of formula II with an acid having a pKa less than 1 and forming a bis salt of formula III:

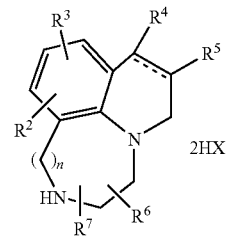

wherein X is a counterion to the acid having a pKa less than 1.
7. The method of claim 6 wherein X is a halogen, hydrogensulfate, or an alkyl- or aryl sulfonate.
8. The method of claim 6 wherein the acid is hydrochloric acid.
9. The method of claim 6 further comprising contacting the bis salt of formula III with a base and forming a free base of formula IV:

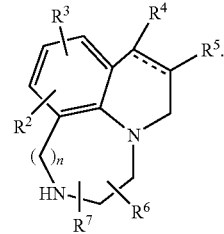

10. The method of claim 9 wherein the base is aqueous sodium hydroxide.
11. The method of claim 9 wherein the free base of formula IV is extracted with an extraction solvent that is immiscible with water.
12. The method of claim 9 further comprising contacting the free base of formula IV with a chiral resolving acid to form a diastereomeric salt.
13. The method of claim 12 wherein the chiral resolving acid is a monofunctional carboxylic acid, difunctional carboxylic acid, sulfonic acid, phosphonic acid, or combinations thereof.
14. The method of claim 12 wherein the free base of formula IV and chiral resolving acid are contacted in the presence of a polar solvent that is capable of dissolving a compound of formula IV:

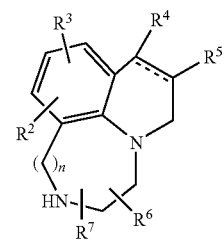

and is capable of crystallizing the diastereomeric salt therefrom.

15. The method of claim 14 wherein the acid is ditoluoyl tartaric acid and the polar solvent comprises isopropanol, ethyl acetate or combinations thereof.

16. The method of claim 12 wherein the diastereomeric salt produced is at least one of formula F:

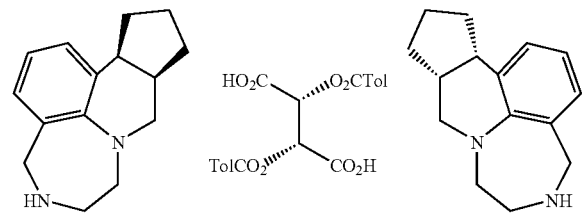

wherein Tol is a toluoyl group.

17. The method of claim 12 further comprising contacting the diastereomeric salt and an acid having a pKa lower than the chiral resolving acid to form a corresponding enantiomeric salt.

18. The method of claim 17 wherein the diastereomeric salt and the acid are contacted in the presence of a polar solvent capable of crystallizing the corresponding enantiomeric salt therefrom.

19. The method of claim 18 wherein the acid is hydrochloric acid and the polar solvent comprises ethyl acetate.

20. The method of claim 17 further comprising crystallizing the enantiomeric salt from a solution comprising aqueous alcohol.

21. The method of claim 17 wherein the enantiomeric salt is at least one compound of formula G:

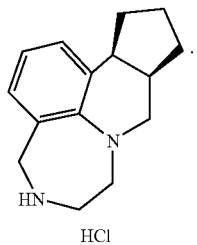

22. The method of claim 1 further comprising contacting the compound of formula II with a base and forming a free base of formula IV:

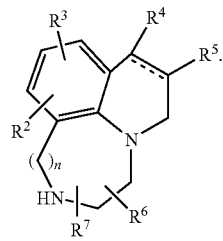

23. The method of claim 22 wherein the base comprises a strong inorganic base.

24. The method of claim 22 wherein the base and compound of formula II are contacted in the presence of a polar solvent.

25. The method of claim 24 wherein the base is potassium hydroxide and the polar solvent comprises methanol.

26. The method of claim 22 further comprising contacting the free base of formula IV with a chiral resolving acid to form a diastereomeric salt.

27. The method of claim 26 wherein the chiral resolving acid is ditoluoyl tartaric acid.

28. The method of claim 26 wherein the diastereomeric salt produced is at least one of formula F:

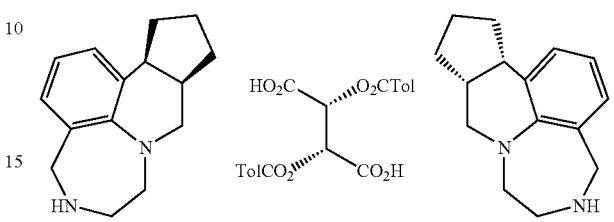

wherein Tol is a toluoyl group.

29. The method of claim 26 further comprising contacting the diastereomeric salt and an acid having a pKa lower than the chiral resolving acid to form a corresponding enantiomeric salt.

30. The method of claim 29 wherein the acid comprises hydrochloric acid, and the diastereomeric salt and the acid are contacted in the presence of a polar solvent that comprises ethyl acetate.

31. The method of claim 29 further comprising crystallizing the enantiomeric salt from a solution comprising an aqueous alcohol.

32. The method of claim 29 wherein the crystallized enantiomeric salt is at least one compound of formula G:

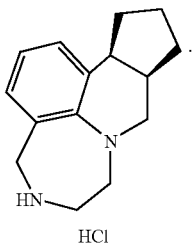

33. A method comprising the steps of:
a) providing a compound of formula I:

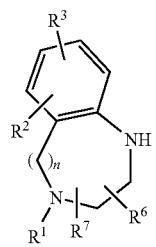

wherein:
$R^2$ and $R^3$ are, independently, hydrogen, hydroxy, alkyl, alkoxy, halogen, carboxamido, carboalkoxy, perfluoroalkyl, cyano, alkanesulfonamido, alkanesulfonyl, alkanamido, amino, alkylamino, dialkylamino, perfluoroalkoxy, alkanoyloxy, alkanoyl, aroyl, aryl, arylalkyl, heteroaryl, or heteroarylalkyl;

$R^6$ and $R^7$ are, independently, hydrogen or alkyl;

n is 1;

b) contacting compound of formula I with at least one formaldehyde equivalent and a reagent having either formula $R^4$—CH=CH—$R^5$ or formula $R^4$—C≡C—$R^5$, in the presence of a Lewis acid and a reaction solvent to form a compound of formula IV:

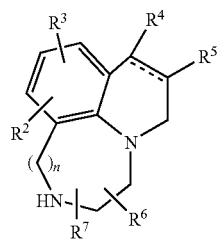

IV wherein:

the formaldehyde equivalent is in solid form at least prior to the contacting;

$R^4$ and $R^5$ are taken together with the carbons to which they are attached, form a cyclic moiety that is cycloalkyl, cycloalkenyl, bridged bicyclic alkyl, bridged bicyclic alkenyl, pyranyl or thiopyranyl in which the sulfur atom is optionally oxidized to the sulfoxide or sulfone; and the dotted line represents an optional double bond.

34. The method of claim 33 wherein the formaldehyde equivalent comprises paraformaldehyde.

35. The method of claim 33 wherein the reaction solvent comprises an alkyl nitrile.

36. The method of claim 33 wherein:

each of $R^2$, $R^3$, $R^6$ and $R^7$ is hydrogen;

n is 1;

$R^4$ and $R^5$, taken together with the carbons to which they are attached, form a cyclopentyl moiety;

the formaldehyde equivalent is paraformaldehyde; and the reaction solvent comprises at least about 90 weight percent acetonitrile.

37. The method of claim 33 further comprising contacting the free base of formula IV with a chiral resolving acid to form a diastereomeric salt.

38. The method of claim 37 wherein the chiral resolving acid is ditoluoyl tartaric acid.

39. The method of claim 37 wherein the diastereomeric salt produced is at least one of formula F:

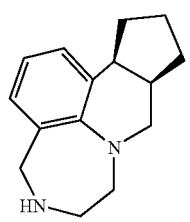 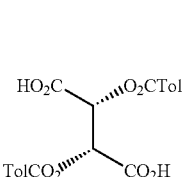 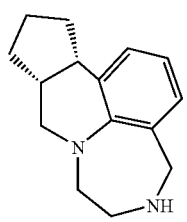

F wherein Tol is a toluoyl group.

40. The method of claim 37 further comprising contacting the diastereomeric salt with an acid having a pKa lower than the chiral resolving acid to form a corresponding enantiomeric salt.

41. The method of claim 40 wherein the acid comprises hydrochloric acid, and the diastereomeric salt and the acid are contacted in the presence of a polar solvent that comprises ethyl acetate.

42. The method of claim 40 further comprising crystallizing the enantiomeric salt from a solution comprising aqueous alcohol.

43. The method of claim 42 wherein the crystallized enantiomeric salt is at least one compound of formula G:

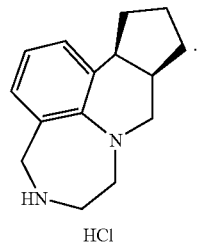

G

44. A composition comprising a diastereomeric salt of a diaroyl-L-tartaric acid and a free base of formula VIb:

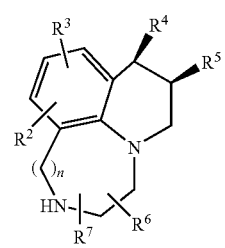

VIb wherein:

$R^2$ and $R^3$ are, independently, hydrogen, hydroxy, alkyl, alkoxy, halogen, carboxamido, carboalkoxy, perfluoroalkyl, cyano, alkanesulfonamido, alkanesulfonyl, alkanamido, amino, alkylamino, dialkylamino, perfluoroalkoxy, alkanoyloxy, alkanoyl, aroyl, aryl, arylalkyl, heteroaryl, or heteroarylalkyl;

$R^4$ and $R^5$ are taken together with the carbons to which they are attached, form a cyclic moiety selected that is cycloalkyl, cycloalkenyl, bridged bicyclic alkyl, bridged bicyclic alkenyl, pyranyl or thiopyranyl in which the sulfur atom is optionally oxidized to the sulfoxide or sulfone;

the dotted line represents an optional double bond;

$R^6$ and $R^7$ are, independently, hydrogen or alkyl; and n is 1.

45. The diastereomeric salt of claim 44 wherein the diaroyl tartaric acid is ditoluoyl-L-tartaric acid.

46. The diastereomeric salt of claim 44 having formula F:

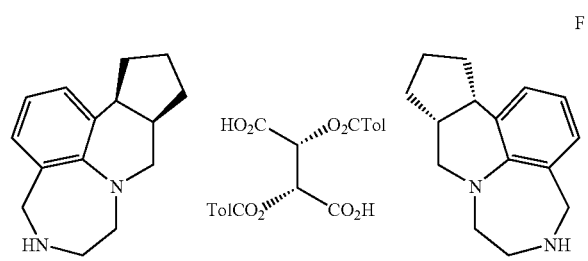

F wherein Tol is a toluoyl group.

47. A composition comprising:

a) at least about 90 area percent HPLC of a compound of formula II:

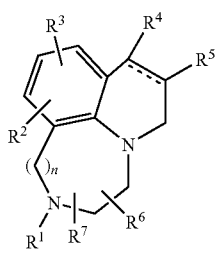

wherein:
R¹ is alkyl, alkanoyl, aroyl, carboalkoxy, or carboalkoxyaryl;
R² and R³ are, independently, hydrogen, hydroxy, alkyl, alkoxy, halogen, carboxamido, carboalkoxy, perfluoroalkyl, cyano, alkanesulfonamido, alkanesulfonyl, alkanamido, amino, alkylamino, dialkylamino, perfluoroalkoxy, alkanoyloxy, alkanoyl, aroyl, aryl, arylalkyl, heteroaryl, or heteroarylalkyl;
R⁴ and R⁵ are taken together with the carbons to which they are attached, form a cyclic moiety selected that is cycloalkyl, cycloalkenyl, bridged bicyclic alkyl, bridged bicyclic alkenyl, pyranyl or thiopyranyl in which the sulfur atom is optionally oxidized to the sulfoxide or sulfone;
the dotted line represents an optional double bond;
R⁶ and R⁷ are, independently, hydrogen or alkyl; and
n is 1; and b) a compound of formula VII:

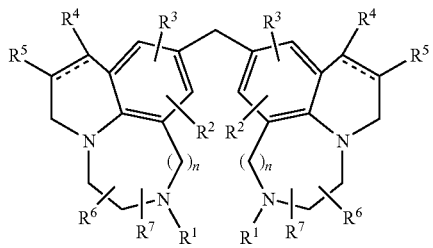

in less than an amount of about 10 area percent HPLC.

48. The composition of claim 47 wherein R¹ is acetyl, R², R³, R⁶ and R⁷ are hydrogen, n is 1, and R⁴ and R⁵, taken together with the carbons to which they are attached, form a cyclopentyl moiety.

49. A composition comprising:
a) a compound of formula III:

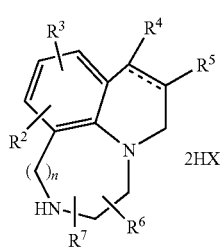

wherein:
R² and R³ are, independently, hydrogen, hydroxy, alkyl, alkoxy, halogen, carboxamido, carboalkoxy, perfluoroalkyl, cyano, alkanesulfonamido, alkanesulfonyl, alkanamido, amino, alkylamino, dialkylamino, perfluoroalkoxy, alkanoyloxy, alkanoyl, aroyl, aryl, arylalkyl, heteroaryl, or heteroarylalkyl;
R⁴ and R⁵ are taken together with the carbons to which they are attached, form a cyclic moiety selected that is cycloalkyl, cycloalkenyl, bridged bicyclic alkyl, bridged bicyclic alkenyl, pyranyl or thiopyranyl in which the sulfur atom is optionally oxidized to the sulfoxide or sulfone;
the dotted line represents an optional double bond;
R⁶ and R⁷ are, independently, hydrogen or alkyl;
n is 1; and
X is counterion to an acid having a pKa less than 1; and b) a compound of formula:

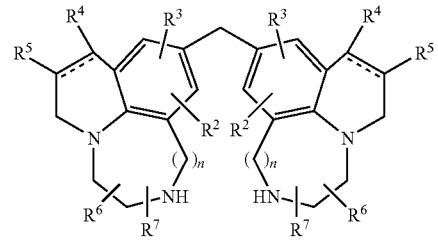

or a salt thereof, in less than an amount of about 10 area percent HPLC.

50. The composition of claim 49 wherein each of R², R³, R⁶ and R⁷ is hydrogen, n is 1, X is Cl, and R⁴ and R⁵, taken together with the carbons to which they are attached, form a cyclopentyl moiety.

51. A composition comprising:
a) a diastereomeric salt of a diaroyl tartaric acid and a free base of formula IV:

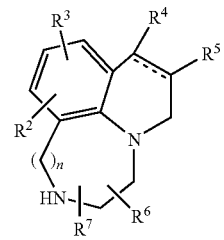

wherein:
R² and R³ are, independently, hydrogen, hydroxy, alkyl, alkoxy, halogen, carboxamido, carboalkoxy, perfluoroalkyl, cyano, alkanesulfonamido, alkanesulfonyl, alkanamido, amino, alkylamino, dialkylamino, perfluoroalkoxy, alkanoyloxy, alkanoyl, aroyl, aryl, arylalkyl, heteroaryl, or heteroarylalkyl;
R⁴ and R⁵ are taken together with the carbons to which they are attached, form a cyclic moiety selected that is cycloalkyl, cycloalkenyl, bridged bicyclic alkyl, bridged bicyclic alkenyl, pyranyl or thiopyranyl in which the sulfur atom is optionally oxidized to the sulfoxide or sulfone;
the dotted line represents an optional double bond;
R⁶ and R⁷ are, independently, hydrogen or alkyl; and
n is 1; and b) a compound of formula

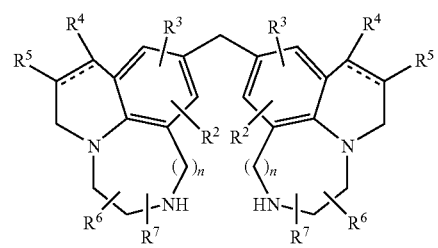

or a salt thereof in an amount of less than about 10 area percent HPLC.

52. The composition of claim 51 wherein the diaroyl tartaric acid is di-p-toluoyl-L-tartaric acid; each of $R^2$, $R^3$, $R^6$ and $R^7$ is hydrogen; n is 1; and $R^4$ and $R^5$, taken together with the carbons to which they are attached, form a cyclopentyl moiety.

53. A composition comprising:
a) a compound of formula G:

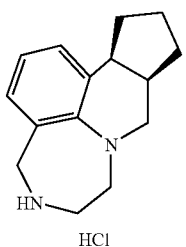

G

HCl and b) one or more organic impurities in a total amount of about 2 area percent HPLC or less, or one or more residual solvents in a total amount of 1.0 weight percent or less, or combinations thereof, wherein the organic impurities or residual solvents comprise at least one of ethanol, ethyl acetate, isopropanol, methanol, or a dimer compound of the formula:

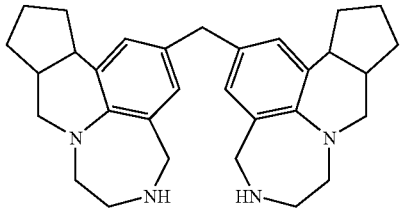

or a salt thereof.

54. A composition comprising:
a) a compound of formula G:

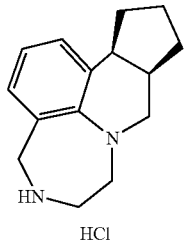

G

HCl and b) one or more organic impurities in a total amount of about 2 area percent HPLC or less, or one or more residual solvents in a total amount of 1.0 weight percent or less, or combinations thereof, wherein the single largest organic impurity is present in an amount of about 0.6 area percent HPLC or less, and wherein the single largest impurity is a compound of the formula:

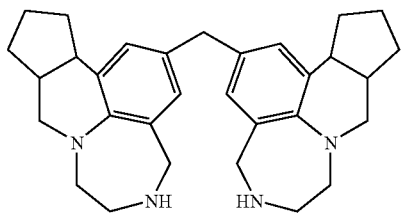

or a salt thereof.

* * * * *